US005965134A

United States Patent [19]

Thiel et al.

[11] Patent Number: 5,965,134
[45] Date of Patent: Oct. 12, 1999

[54] IMMUNOGENIC COMPOSITION AGAINST CLASSICAL SWINE FEVER VIRUS (CSFV)

[75] Inventors: Heinz-Jürgen Thiel, Giessen; Knut Elbers; Thomas Pauly, both of Tübingen, all of Germany

[73] Assignee: Akzo Nobel, N.V., Arnhem, Netherlands

[21] Appl. No.: 08/937,102

[22] Filed: Sep. 24, 1997

Related U.S. Application Data

[63] Continuation of application No. 08/693,247, filed as application No. PCT/EP95/05066, Dec. 20, 1995, abandoned.

[30] Foreign Application Priority Data

Dec. 20, 1994 [EP] European Pat. Off. .............. 94203696

[51] Int. Cl.$^6$ ............................ A61K 39/12; C12N 15/00
[52] U.S. Cl. ..................................... 424/186.1; 424/199.1; 424/204.1; 424/200.1; 424/218.1; 424/220.1; 424/229.1; 435/320.1; 530/300; 536/23.72
[58] Field of Search .............................. 424/194.1, 186.1, 424/204.1, 200.1, 218.1, 220.1, 199.2, 229.1; 435/320.1; 530/300; 536/23.72

[56] References Cited

PUBLICATIONS

T.G. Kimman et al., *Journal of Virology*, 67:5:2922–2927, 1993.
T. Pauly et al., *Journal of General Virology*, 76:3039–3049, 1995.

*Primary Examiner*—Mary E. Mosher
*Assistant Examiner*—Ali R. Salimi
*Attorney, Agent, or Firm*—Mary E. Gormley

[57] ABSTRACT

This application is concerned with immunogenic polypeptides of pestiviruses, specifically Classical Swine Fever Virus (CVFV), specifically the nonstructural protein p10, more specifically T-cell epitopes from this protein and nucleic acid molecules encoding these polypeptides, and vaccines and diagnostics with these polypeptides or nucleic acid molecules.

13 Claims, 6 Drawing Sheets

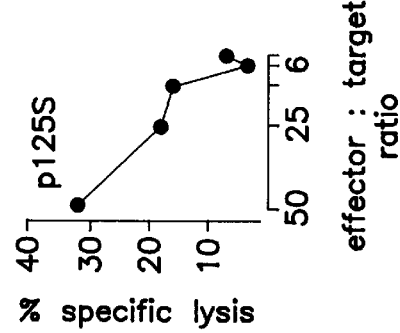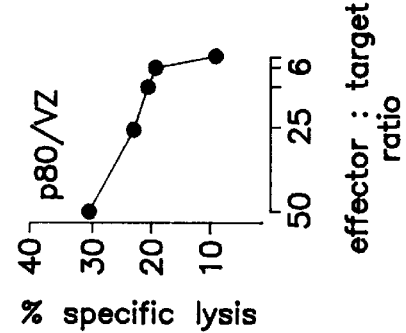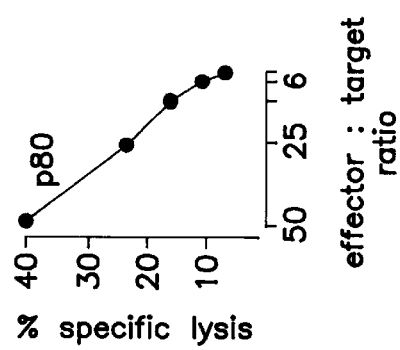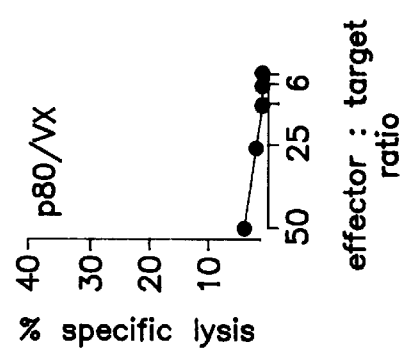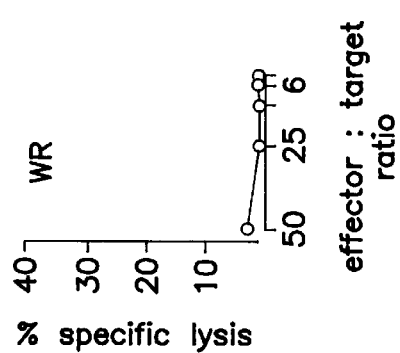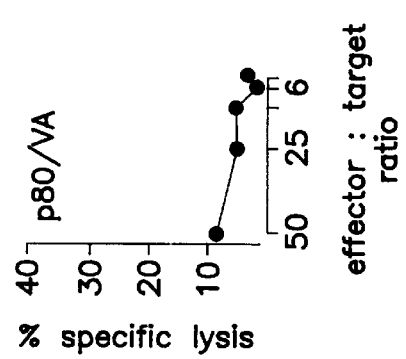

% specific lysis

| SEQ ID | Sequence | Bar |
|---|---|---|
| [SEQ ID NO:7] | WGLSTAEN | ~13 |
| [SEQ ID NO:8] | VGLSTAENA | ~12 |
| [SEQ ID NO:9] | GLSTAENAL | ~7 |
| [SEQ ID NO:10] | LSTAENALL | ~8 |
| [SEQ ID NO:11] | STAENALLV | ~8 |
| [SEQ ID NO:12] | TAENALLVA | ~13 |
| [SEQ ID NO:13] | AENALLVAL | ~18 |
| [SEQ ID NO:6] | ENALLVALF | ~30 |
| [SEQ ID NO:14] | NALLVALFG | ~2 |
| [SEQ ID NO:15] | ALLVALFGY | ~3 |
| [SEQ ID NO:16] | LLVALFGYV | ~5 |
| [SEQ ID NO:17] | LVALFGYVG | ~2 |
| NON-INFECTED | | ~0 |
| CSFV-INFECTED | | ~40 |

FIG. 5

IMMUNOGENIC COMPOSITION AGAINST CLASSICAL SWINE FEVER VIRUS (CSFV)

This is a continuation of application Ser. No. 08/693,247 filed Aug. 16, 1996, now abandoned, which is a 371 of PCT/EP95/05066 filed Dec. 20, 1995.

FIELD OF THE INVENTION

This application is concerned with polypeptides comprising T lymphocyte stimulatory proteins of pestiviruses, especially Classical Swine Fever Virus (CSFV), specifically the nonstructural protein p10, more specifically T cell epitopes from this protein, and nucleic acids coding for these polypeptides, recombinant vectors with these nucleic acids, host cells transformed with these vectors, vaccines and diagnostics with this polypeptides and processes for preparing them.

BACKGROUND OF THE INVENTION

The genus pestivirus belongs to the family of Flaviviridae and consists of Classical Swine Fever Virus (or hog cholera virus), which is the causative agent of classical swine fever bovine viral diarrhoea virus (BVDV) infectious to cattle and border disease virus (BDV) infectious to sheep.

Pestiviruses are small enveloped RNA viruses having a diameter of 40–60 nm. The virions consist of a nuclear capsid enveloped by a lipid layer embedded with glycoproteins. The genome of pestiviruses consists of a single stranded RNA of approximately 12.5 kB. It contains a single open reading frame (ORF) which is flanked by parts that are not translated. The 3' end is not polyadenylated.

Viral proteins are formed by co- and posttranslational processing of a hypothetic polyprotein, while the structural proteins are coded in the 5' end of the genome. In contrast to other flaviviridae the pestiviruses have a sequence coding for a non-structural p23 protein at the 5' end. This N-terminal protease (Npro) is spliced from the next protein by an autoproteolytical process. In the 3' direction the sequence coding for a p14 nuclear capsid and a signal sequence, which is responsible for the translocation of the subsequent sequences for glycoprotein E0, E1 and E2 in the lumen of the endoplasmatic reticulum (ER), are following. The splicing of the single glycoproteins probably is caused by cellular signalases in the ER. The glycoproteins can form complex structures in infected cells by dimensioning through S-S-bridges. The function of these complex structures is not yet known.

Next to the sequences for the structural proteins the sequences for the non-structural proteins p125, p10, p30 and p133 are found in the polyprotein. Analogous to posttranslational processes in cytopathogenic Bovine Viral Diarrhea Virus (BVDV, another pestivirus) anp 80 protein can be detected after processing the p125 protein (Desport, M. and Brownlie J., Arch. Virol. Suppl. 3, 261–265, 1991). The p133 non-structural protein, which is processed into p58 and p75 proteins, contains sequence motifs which resemble RNA polymerase sequences. The amino acid sequences of the non-structural CSFV proteins are considered to be approximately: 3-1142 (p125), 1143–1206 (p10) shown in SEQ ID NO: 1 and 2 herein. The putative N-terminus of p80 is amino acid no. 460 (SEQ ID NO: 1 and 2). The start of p30 is also shown in SEQ ID NO. 1 and 2, i.e. amino acid number 1207. The complete sequence of p30 for CSFV Alfort shown in Meyers et al. (Virology 171, 555–567, 1989; FIG. 4 amino acids 2337–2683). The DNA sequences encoding these proteins are also shown in SEQ ID NO. 1 herein and in Meyers et al. (supra).

On infection with CSFV acute, peracute, chronic or clinical invisible symptoms can occur. The severity of the disease is dependent on the infectious load on one hand, and on the other hand the age of the animal, the immune competence and total constitution of the animal form important factors.

In the peracute illness, which results in the death of the animal after three to five days after infection with a highly virulent strain (e.g. the CSFV-Brescia strain), only a fever is observable. In the acute disease state, next to a high temperature, leucopenia, conjunctivitis and loss appetite are observable. In the final stage of the disease central nervous system disturbances occur. Further characteristics are an atrophy of the thymus, cyanosis of the skin and cutaneous haemorrhages, partially caused by a thrombocytopenia. Mortality of the disease in the acute phase is 30–100%.

The chronic disease form is found after infection with mesogenic virus strains. This form is most dangerous when piglets are infected in utero by diaplacental infection. After birth these piglets only survive for 6–8 weeks during which time they form a source of infection.

Pigs that survive a postnatal infection, gain lifetime immunity, which probably results from an induction of the humoral immune response. Neutralising antibodies are found after two to three weeks after infection.

Several vaccines have been developed for this economically important disease. Vaccines with inactivated virus give only shortlasting protection and are not used anymore (Biront, P. and Leunen, J., in: Liess, B. (ed.): Classical swine fever and related viral infections. Martinus Nijhoff Publ., Boston pp. 181–200, 1988). Better protection has been established with attenuated viruses obtained by serial passaging in rabbits (C-strains) or in cell cultures (e.g. Thiverval-strain) (Launais, M. et al., Rev. Med. Vet., 123, 1537–1554, 1972; Shimizu Y., Jap. J. Trop. Agr. Res. Sci., 13, 167–170, 1980).

However, a disadvantage of these vaccines is that they do not discern between vaccinated animals and animals infected with a field virus. In the European Community, therefore, use of these vaccines is forbidden presently and control of classical swine fever is established by isolation and slaughtering of infected swine.

In recent years some results have been obtained with live vaccines based on recombinant viruses (van Zijl, M. et al., J. Virol. 65, 2761–2765, 1991; Rumenapf. T. et al., J. Virol. 65, 589–597, 1991; Hulst, M. M. et al., J. Virol. 67, 5435–5442, 1993). These vaccines have all been based on the expression of structural glycoproteins in recombinant vector viruses.

SUMMARY OF THE INVENTION

The invention present is directed to a polypeptide comprising a pestivirus T lymphocyte stimulatory protein, or an immunogenically active part thereof.

Such a polypeptide is essentially free from other pestiviral proteins with which it is ordinarily associated. Specifically the T lymphocyte stimulatory protein is a Classical Swine Fever Virus T lymphocyte stimulatory protein, or an immunogenically active part thereof.

More specifically the polypeptide comprises the CSFV non-structural p10 protein. Because the CSFV proteins are expressed by the virus as a polyprotein which is cleaved subsequent to translation, also polypeptides comprising the p10 protein and its flanking protein(s) p125 and/or p30 or parts thereof are contemplated herein.

More specifically the polypeptide comprises a T cell epitope with the amino acid sequence S-T-A-E-N-A-L-L-V-A-L-F-G-Y-V (SEQ ID NO:4), most specifically the polypeptide comprises a T cell epitope with the amino acid sequence E-N-A-L-L-V-A-L-F (SEQ ID NO:6).

In general, the term "protein" refers to a molecular chain of amino acids with biological activity. A protein is not of a specific length and can, if required, be modified in vivo or in vitro, by, for example, glycosylation, amidation, carboxylation or phosphorylation; thus, inter alia, peptides, oligopeptides and polypeptides are included within the definition.

DETAILED DESCRIPTION OF THE INVENTION

More particularly, this invention provides polypeptides comprising T-lymphocyte stimulatory proteins, or immunogenically active parts thereof, which comprise the amino acid sequence shown in SEQ ID NO. 2 and their biologically functional equivalents or variants.

Immunogenically active parts of these polypeptides are those parts of the amino acid sequence that are able to elicit a T cell activation.

More specifically this invention includes polypeptides, which comprise the amino acid sequence shown in SEQ ID NO: 6 and still more specifically are polypeptides which comprise the amino acid sequence shown in SEQ ID NO: 4.

The biologically functional equivalents or variants of the proteins specifically disclosed herein are proteins derived from the above noted amino acid sequences, for example by deletions, insertions and/or substitutions of one or more amino acids, but retain one or more immunogenic determinants of CSFV, i.e. said variants have one or more epitopes capable of eliciting an immune response in a host animal.

It will be understood that, for the particular proteins embraced herein, natural variations can exist between individual virus strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred Frequently in evolution are, inter alia, Ser/Ala, Ser/Gly, Asp/Gly, Asp/Asn, Ile/Val (see Dayhof, M.D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science, 227, 1435–1441, 1985) and determining the functional similarity between homologous proteins. Such amino acid substitutions of the exemplary embodiments of this invention are within the scope of the invention as long as the resulting proteins retain their immunoreactivity.

The preparation of the proteins according to the invention is effected by means of one of the known organic chemical methods for peptide synthesis or with the aid of recombinant DNA techniques.

The organic chemical methods for peptide synthesis are considered to include the coupling of the required amino acids by means of a condensation reaction, either in homogenous phase or with the aid of a so-called solid phase.

The most common methods for the above condensation reactions are: the carbodiimide method, the azide method, the mixed anhydride method and the method using activated esters, such as described in The Peptides, Analysis, Synthesis, Biology Vol. 1–3 (Ed.: Gross, E. and Meienhofer, J.) 1979, 1980, 1981 (Academic Press, Inc.).

Preparation of suitable fragments of above-mentioned peptides according to the invention using the "solid phase" is for instance described in J. Amer. Chem. Soc. 85, 2149 (1963) and Int. J. Peptide Protein Res. 35, 161–219 (1990. The coupling of the amino acids of the peptide to be prepared usually starts from the carboxyl end side. For this method a solid phase is needed on which there are reactive groups or on which such groups can be introduced. This can be, for example a copolymer of benzene and divinylbenzene with reactive chloromethyl groups, or a polymeric solid phase rendered reactive with hydroxymethyl or amine-function.

A particularly suitable solid phase is, for example, the p-alkoxybezyl alcohol resin (4-hydroxy-methyl-phenoxy-methyl-copolystyrene-1% divinylbenzene resin), described by Wang, J. Am. Chem. Soc. 95, 1328 (1974). After synthesis the peptides can be split from this solid phase under mild conditions.

In order to determine if any protein and which was responsible for a T cell mediated effect, CSFV infected target cells were cultured in the following way: from a miniature swine ("NIH-Minipig"; MHC$^{d/d}$ haplotype) a kidney was removed and cut to pieces under sterile conditions. The organ pieces were rinsed with PBS and pieces were pipetted in a culture flask. They were incubated in culture medium to which a collagenase-dispase solution was added. The cells were rinsed from the tissue with PBS, pelleted and washed and further cultivated.

For obtaining a stable, transformed cell line the cells were transformed with a plasmid having the sequence for the "large T" antigen of SV-40 (Southern, P. and Berg, P., J. Molec. Appl. Genetics., 1, 327–341, 1982; Fanning, E., J. Virol., 66, 1289–1293, 1992). The MAX-cells thus obtained were selected by culturing with a neomycin analogon G418 (Boehringer) and tested for mycoplasma contamination (Mycoplasma Detection Kit, Boehringer Mannheim). The MAX cells were cultured in DMEM and were infected with CSFV.

To screen the genome of CSFV for epitopes recognized by virus specific T lymphocytes, autologous MAX cells were infected with Vaccinia virus/CSFV recombinants expressing different viral proteins. Successful infection of target cells with the recombinants was routinely checked by the cytopathogenic effect of Vaccinia virus. In addition the expression of CSFV proteins was demonstrated by immunocytochemical studies and western-blot analysis of infected MAX cells.

Effector cells obtained from immunized miniature swine were cocultivated with Vaccinia virus recombinant infected radiolabeled targets (or Vaccinia virus wildtype infected targets as a control) at different effector to target ratios for 4 hours. After centrifugation 100 µl of each supernatant were collected and the chromium release determined as cpm in a gamma radiation counter. Percent specific lysis was calculated by the formula:

$$\% \text{ specific lysis} = \frac{(\text{exp. cpm} - \text{spont. cpm}) * 100}{(\text{total cpm} - \text{spont. cpm})}$$

Target cell controls were included in the following way: in order to measure spontaneous radioisotope release (spont. cpm), target cells were incubated without effectors. In addition, the total chromium incorporation in target cells was determined (total cpm).

In this way CSFV-specific CTL were identified. For a further characterization of the epitopes responsible for the effects a series of overlapping peptides was synthesized. These peptides were loaded onto the MAX target cells by incubation in wells of round bottom plates for 1 hour. Effector cells were then added to achieve an effector to target cell ratio of 100:1. The plates were centrifuged and incubated and the specific lysis was determined by measuring chromium release as described above.

According to a second aspect of the invention, there is provided a nucleic acid sequence encoding all or a substantial part, in particular the immunologically active part, of a purified pestivirus T lymphocyte stimulatory protein, more specifically a CSFV T cell stimulatory protein.

A nucleic acid sequence according to the present invention may be isolated from a particular CSFV strain and multiplied by recombinant DNA techniques including polymerase chain reaction (PCR) technology or may be chemically synthesized in vitro by techniques known in the art.

The invention further provides isolated and purified nucleic acid sequences encoding the above mentioned proteins of CSFV. Such nucleic acid sequences are shown in SEQ. ID. NO: 1, SEQ ID NO: 3 and SEQ ID NO: 5. It is well known in the art that the degeneracy of the genetic code permits substitution of bases in the codon resulting in another codon but still coding for the same amino acid, e.g. the codon for the amino acid glutamic acid is both GAT and GAA. Consequently, it is clear that, for the expression of a protein with the amino acid sequence shown in SEQ. ID. NO: 2, the nucleic acid sequence may have a codon composition different from the nucleic acid sequence shown in SEQ. ID. NO: 1.

Such a nucleic acid sequence may be operatively linked to various replication sequences with which it is not associated, or linked in nature, resulting in a so-called recombinant vector which can be used for the transfection of a suitable host. Useful recombinant vectors are preferably derived from plasmids, bacteriophages, cosmids or viruses.

Specific vectors or cloning vehicles which can be used to clone nucleic acid sequences according to the invention are known in the art and include inter alia plasmid vectors such as pBR322, the various pUC, pGEM and Bluescript plasmids; bacteriophages, e.g. lambdagt-Wes, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., *Arch. Virol.*, 110, 1–24, 1990). The methods to be used for the construction of a recombinant vector according to the invention are known to those of ordinary skill in the art and are inter alia set forth in Maniatis, T. et al. (Molecular Cloning A Laboratory Manual, second edition; Cold Spring Harbor Laboratory, 1989).

For example, the insertion of the nucleic acid sequence according to the invention into a cloning vector can easily be achieved when both the genes and the desired cloning vehicle have been cut with the same restriction enzyme(s) as complementary DNA termini are thereby produced.

Alternatively, it may be necessary to modify the restriction sites that are produced into blunt ends either by digesting the single-stranded DNA or by filling in the single-stranded termini with an appropriate DNA polymerase. Subsequently, blunt end ligation with an enzyme such as T4 DNA ligase may be carried out.

If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

"Transformation", as used herein, refers to the introduction of an heterologous nucleic acid sequence into a host cell, irrespective of the method used, for example direct uptake or transduction. The heterologous nucleic acid sequence may be maintained through autonomous replication or, alternatively, may be integrated into the host genome. If desired, the recombinant vectors are provided with appropriate control sequences compatible with the designated host. These sequences can regulate the expression of the inserted nucleic acid sequence. In addition to microorganisms, cell cultures derived from multicellular organisms may also be used as hosts.

The recombinant vectors according to the invention preferably contain one or more marker activities that may be used to select for desired transformants, such as ampicillin and tetracycline resistance in pBR322, ampicillin resistance and Â-peptide of β-galactosidase in pUC8.

A suitable host cell is a microorganism or cell which can be transformed by a nucleic acid sequence encoding a polypeptide or by a recombinant vector comprising such a nucleic acid sequence, and which can, if desired, be used to express said polypeptide encoded by said nucleic acid sequence. The host cell can be of prokaryotic origin, e.g. bacteria such as *Escherichia coli, Bacillus subtilis* and Pseudomonas species; or of eukaryotic origin such as yeasts, e.g. *Saccharomyces cerevisiae* or higher eukaryotic cells such as insect, plant or mammalian cells, including HeLa cells and Chinese hamster ovary (CHO) cells. Insect cells include the Sf9 cell line of *Spodoptera frugiperda* (Luckow et al., *Biotechnology* 6, 47–55, 1988). Information with respect to the cloning and expression of the nucleic acid sequence of the present invention in eukaryotic cloning systems can be found in Esser, K. et al. (Plasmids of Eukaryotes, Springer-Verlag, 1986).

As host organism also other viruses can be used, which are able to express the inserted pestivirus sequence. Such viruses are commonly denoted vector viruses.

In general, prokaryotes are preferred for the construction of the recombinant vectors useful in the present invention. *E.coli* K12 strains are particularly useful, especially DH5a or MC1061 strains.

For expression, nucleic acid sequences of the present invention are introduced into an expression vector, i.e. said sequences are operably linked to expression control sequences.

Such control sequences may comprise promoters, enhancers, operators, inducers, ribosome binding sites etc. Therefore, the present invention provides a recombinant vector comprising a nucleic acid sequence encoding a CSFV protein identified above operably linked to expression control sequences, which is capable of expressing the DNA sequences contained therein in (a) transformed host cell(s) or organism.

It should be understood, of course, that the nucleotide sequences inserted at the selected site of the cloning vector may include nucleotides which are not part of the actual structural gene for the desired polypeptide, or may include only a fragment of the complete structural gene for the desired protein as long as the transformed host will produce a polypeptide having at least one or more immunogenic determinants of a CSFV protein antigen.

When the host cells are bacteria, useful expression control sequences which may be used include the Trp promotor and operator (Goeddel, et al., *Nucl. Acids Res.,* 8, 4057, 1980); the lac promotor and operator (Chang, et al., *Nature,* 275, 615, 1978); the outer membrane protein promotor (Nakamura, K. and Inouge, M., *EMBO J.,* 1, 771–775, 1982); the bacteriophage lambda promoters and operators (Remaut, E. et al., *Nucl. Acids Res.,* 11, 4677–4688, 1983); the Â-amylase (*B. subtilis*) promotor and operator, termination sequences and other expression enhancement and control sequences compatible with the selected host cell. When the host cell is yeast, illustrative useful expression control sequences include, e.g., Â-mating factor. For insect cells the polyhedrin or p10 promoters of baculoviruses can be used (Smith, G. E. et al., *Mol. Cell. Biol.* 3, 2156–65, 1983). When the host cell is of mammalian origin illustrative useful expression control sequences include the SV-40 promotor (Berman, P. W. et al., *Science,* 222, 524–527, 1983) or the metallothionein promotor (Brinster, R. L., *Nature,* 296, 39–42, 1982) or a heat shock promotor (Voellmy et al., *Proc. Natl. Acad. Sci. USA,* 82, 4949–53, 1985). Alternatively, expression control sequences present in CSFV may also be applied. For maximizing gene expression, see also Roberts and Lauer (*Methods in Entomology,* 68, 473, 1979).

Therefore, the invention also comprises (a) host cell(s) or organism(s) having a nucleic acid sequence or a recombinant nucleic acid molecule or a recombinant vector described above, capable of producing the pestivirus protein by expression of the nucleic acid sequence.

Immunization of animals against pestivirus infection, especially swine against CSFV, can be achieved by administering to the animals a polypeptide according to the invention in animmunologically relevant context as a subunit vaccine. The subunit vaccine according to the invention may comprise a polypeptide in a pure form, optionally in the presence of a pharmaceutically acceptable carrier. The polypeptide can optionally be covalently bonded to a non-related protein, which can be of advantage in the purification of the fusion product. Examples are β-galactosidase, protein A, prochymosine, blood clotting factor Xa, etc.

In some cases the ability to raise protective immunity using these polypeptides per se may be low. Small fragments are preferably conjugated to carrier molecules in order to raise their immunogenicity. Suitable carriers for this purpose are macromolecules, such as natural polymers (proteins like key hole limpet hemocyanin, albumin, toxins), synthetic polymers like polyamino acids (polylysine, polyalanine), or micelies of amphiphilic compounds like saponins and palmitinic acid. Alternatively these fragments may be provided as polymers thereof, preferably linear polymers.

If required, the proteins according to the invention which are to be used in a vaccine can be modified in vitro or in vivo, for example by glycosylation, amidation, carboxylation or phosphorylation.

The immunological system will even be more effectively triggered when the vaccine comprises the polypeptides as presented in an MHC molecule by an antigen presenting cell (APC). Antigen presentation can be achieved by using monocytes, macrophages, interdigitating cells, Langerhans cells and especially dendritic cells, loaded with one of the peptides of the invention. Loading of the APC's can be accomplished by bringing the polypeptides of the invention into or in the neighbourhood of the APC, but it is more preferable to let the APC process the complete antigen. In this way a presentation is achieved which mimicks the in vivo situation the most realistic. Furthermore the MHC used by the cell is of the type which is suited to present the epitope.

An overall advantage of using APC's for the presentation of the epitopes is the choice of APC cell that is used in this respect. It is known from different types of APC's that there are stimulating APC's and inhibiting APC's.

Preferred are the listed cell types, which are so-called 'professional' antigen presenting cells, characterized in that they have co-stimulating molecules, which have an important function in the process of antigen presentation. Such co-stimulating molecules are, for example, B7, CTLA-4, CD70 or heat stable antigen.

Fibroblasts, which have also been shown to be able to act as an antigen presenting cell, lack these co-stimulating molecules.

It is also possible to use cells already transfected with a cloning vehicle harbouring the information for the polypeptides of the invention and which are cotransfected with a cloning vehicle which comprises the nucleotide sequence for an MHC molecule. These cells will act as an antigen presenting cell and will present pestivirus epitopes in the MHC molecules which are expressed on their surface. It is envisaged that this presentation will be enhanced, when the cell is also capable of expressing one of the abovementioned co-stimulating molecules, or a molecule with a similar function. This expression can be the result of transformation or transfection of the cell with a third cloning vehicle having the sequence information coding for such a co-stimulating molecule, but it can also be that the cell already was capable of production of co-stimulating molecules.

In stead of a vaccine with these cells, which next to the desired expression products, also harbour many elements which are also expressed and which can negatively affect the desired immunogenic reaction of the cell, it is also possible that a vaccine is composed with liposomes which expose MHC molecules loaded with peptides, and which, for instance, are filled with lymphokines. Such liposomes will trigger a immunologic T cell reaction.

By presenting the peptide in the same way as it is also presented in vivo an enhanced T cell response will be evoked. Furthermore, by the natural adjuvant working of the, relatively large, antigen presenting cells also a B cell response is triggered. This B cell response will among other things lead to the formation of antibodies directed to the peptide-MHC complex. It is this naturally occurring phenomenon which is enlarged by the vaccination of APC's already presenting the peptides of the invention. By enlarging not only an enlarged T cell response will be evoked, but also a B cell response which leads to antibodies directed to the MHC-peptide complex will be initiated.

An alternative to subunit vaccines is live vaccines. A nucleic acid sequence according to the invention is introduced by recombinant DNA techniques into a host cell or organism (e.g. a bacterium or virus) in such a way that the recombinant host is still able to replicate, thereby expressing a polypeptide coded by the inserted nucleic acid sequence and eliciting an immune response in the infected host swine.

A preferred embodiment of the present invention is a recombinant vector virus comprising a heterologous nucleic acid sequence described above, capable of expressing the DNA sequence in (a) host cell(s) or host swine infected with the recombinant vector virus. The term "heterologous" indicates that the nucleic acid sequence according to the invention is not normally present in nature in the vector virus.

Furthermore, the invention also comprises (a) host cell(s) or cell culture infected with the recombinant vector virus, capable of producing the CSFV protein by expression of the nucleic acid sequence.

For example the well known technique of in vivo homologous recombination can be used to introduce an heterologous nucleic acid sequence according to the invention into the genome of the vector virus.

First, a DNA fragment corresponding with an insertion region of the vector genome, i.e. a region which can be used for the incorporation of an heterologous sequence without disrupting essential functions of the vector such as those necessary for infection or replication, is inserted into a cloning vector according to standard recDNA techniques. Insertion regions have been reported for a large number of microorganisms (e.g. EP 80,806, EP 110,385, EP 83,286, EP 314,569, WO 88/02022, WO 88/07088, U.S. Pat. No. 4,769,330 and U.S. Pat. No. 4,722,848).

Second, if desired, a deletion can be introduced into the insertion region present in the recombinant vector molecule obtained from the first step. This can be achieved for example by appropriate exonuclease III digestion or restriction enzyme treatment of the recombinant vector molecule from the first step.

Third, the heterologous nucleic acid sequence is inserted into the insertion region present in the recombinant vector of the first step or in place of the DNA deleted from said recombinant vector. The insertion region DNA sequence should be of appropriate length as to allow homologous recombination with the vector genome to occur. Thereafter, suitable cells can be infected with wild-type vector virus or transformed with vector genomic DNA in the presence of the recombinant vector containing the insertion flanked by appropriate vector DNA sequences whereby recombination occurs between the corresponding regions in the recombinant vector and the vector genome. Recombinant vector progeny can now be produced in cell culture and can be selected for example genotypically or phenotypically, e.g. by hybridization, detecting enzyme activity encoded by a gene co-integrated along with the heterologous nucleic acid sequence, or detecting the antigenic heterologous polypeptide expressed by the recombinant vector immunologically.

Next, these recombinant microorganisms can be administered to swine for immunization whereafter they maintains themselves for some time, or even replicate in the body of the inoculated animal, expressing in vivo a polypeptide coded for by the inserted nucleic acid sequence according to the invention resulting in the stimulation of the immune system of the inoculated animal. Suitable vectors for the incorporation of a nucleic acid sequence according to the invention can be derived from viruses such as pox viruses, e.g. vaccinia virus (EP 110,385, EP 83,286, U.S. Pat. No. 4,769,330 and U.S. Pat. No. 4,722,848), herpes viruses such as Aujeszky virus (van Zijl, M. et al., *J. Virol.* 62(6), 2191–2195, 1988), porcine respiratory syncitiae virus, adeno virus or influenza virus, or bacteria such as *E. coli, Streptococcus suis, Actinobacillus pleuropneumoniae* or specific Salmonella species. With recombinant microorganisms of this type, the polypeptide synthesized in the host animal can be exposed as a surface antigen. In this context fusion of the polypeptide with OMP proteins, or pilus proteins of for example *E. coli* or synthetic provision of signal and anchor sequences which are recognized by the organism are conceivable. It is also possible that the pestivirus polypeptide, if desired as part of a larger whole, is released inside the animal to be immunized. In all of these cases it is also possible that one or more immunogenic products will find expression which generate protection against various pathogens and/or against various antigens of a given pathogen.

A vector vaccine according to the invention can be prepared by culturing a recombinant bacterium or a host cell infected with a recombinant vector comprising a nucleic acid sequence according to the invention, whereafter recombinant bacteria or vector containing cells and/or recombinant vector viruses grown in the cells can be collected, optionally in a pure form, and formed into a vaccine optionally in a lyophilised form.

Host cells transformed with a recombinant vector according to the invention can also be cultured under conditions which are favourable for the expression of a polypeptide coded by said nucleic acid sequence. Vaccines may be prepared using samples of the crude culture, host cell lysates or host cell extracts, although in another embodiment more purified polypeptides according to the invention are formed into a vaccine, depending on its intended use. In order to purify the polypeptides produced, host cells transformed with a recombinant vector according to the invention are cultured in an adequate volume and the polypeptides produced are isolated from such cells, or from the medium if the protein is excreted. Polypeptides excreted into the medium can be isolated and purified by standard techniques, e.g. salt fractionation, centrifugation, ultrafiltration, chromatography, gel filtration or immunoaffinity chromatography, whereas intracellular polypeptides can be isolated by first collecting said cells, disrupting the cells, for example by sonication or by other mechanically disruptive means such as French press, followed by separation of the polypeptides from the other intracellular components and forming the polypeptides into a vaccine. Cell disruption could also be achieved by chemical (e.g. EDTA or detergents such as Triton X114) or enzymatic means, such as lysozyme digestion.

It is also possible to vaccinate animals with the "nude" DNA, i.e. the nucleic acids as defined above without any regulatory sequences. This DNA then will be incorporated in the genome of the vaccinated animal and thus express the polypeptide of the invention.

The vaccines according to the invention can be enriched by numerous compounds which have an enhancing effect on the initiation and the maintenance of both the T cell and the B cell response after vaccination.

In this way addition of cytokines to the vaccine will enhance the T cell response. Suitable cytokines are for instance interleukines, such as IL-2, IL-4, IL-7, or IL-12, GM-CSF, RANTES, tumor necrosis factor and interferons, such as IFN-gamma.

Antibodies or antiserum directed against a polypeptide according to the invention have a potential use in passive immunotherapy, diagnostic immunoassays and generation of anti-idiotypic antibodies.

The vaccine according to the invention can be administered in a conventional active immunization scheme: single or repeated administration in a manner compatible with the dosage formulation, and in such amount as will be prophylactically effective, i.e. the amount of immunizing antigen or recombinant microorganism capable of expressing said antigen that will induce immunity in swine against challenge by virulent CSFV. It can also be given in addition to a conventional (B lymphocyte directed) vaccination to enhance the immunity caused by such a vaccination. Immunity is defined as the induction of a significant level of protection in a population of animals after vaccination compared to an unvaccinated group.

For live viral vector vaccines the dose rate per animal may range from $10^3$–$10^8$ typical subunit vaccine according to the invention comprises 1 µg–1 mg of the protein according to the invention. Such vaccines can be administered intradermally, subcutaneously, intramuscularly, intraperitoneally, intravenously, orally or intranasally.

Additionally the vaccine may also contain an aqueous medium or a water containing suspension, often mixed with other constituents in order to increase the activity and/or the shelf life. These constituents may be salts, pH buffers, stabilizers (such as skimmed milk or casein hydrolysate), emulsifiers, adjuvants to improve the immune response (e.g. oils, muramyl dipeptide, aluminium hydroxide, saponin, polyanions and amphipatic substances) and preservatives.

It is clear that a vaccine according to the invention may also contain immunogens related to other pathogens of swine, or may contain nucleic acid sequences encoding these immunogens, like antigens of *Actinobacillus pleuropneumoniae*, Pseudorabies virus, Porcine Influenza virus, Porcine Parvovirus, *Streptococcus suis*, Transmissible Gastroenteritisvirus, Rotavirus, *Escherichia coli, Erysipelothrix rhusiopathiae, Pasteurella multocida* and *Bordetella bronchiseptica*.

The invention also relates to an "immunochemical reagent", which reagent comprises a protein according to the invention. The term "immunochemical reagent" signifies that the protein according to the invention is bound to a suitable support or is provided with a labelling substance.

The supports that may be used are, for example, the inner wall of a microtest well or a cuvette, a tube or capillary, a membrane, filter, test strip or the surface of a particle such as for example, a latex particle, an erythrocyte, a dye sol, a metal sol or metal compound as sol particle.

Labelling substances which can be used are, inter alia, a radioactive isotope, a fluorescent compound, an enzyme, a dye sol, metal sol or metal compound as sol particle.

A nucleic acid sequence according to the invention can also be used to design specific probes for hybridization experiments for the detection of pestivirus related nucleic acids in any kind of tissue.

The present invention also comprises a test kit comprising said nucleic acid sequence useful for the diagnosis of pestivirus, specifically CSFV infection.

The invention also relates to a test kit to be used in an immunoassay, this test kit containing at least one immunochemical reagent according to the invention. The immunochemical reaction which takes place using this test kit is preferably a sandwich reaction, an agglutination reaction, a competition reaction or an inhibition reaction.

For carrying out sandwich reaction, the test kit can consist, for example, of a polypeptide according to the invention bonded to a solid support, for example the inner wall of a microtest well, and either a labelled polypeptide according to the invention or a labelled anti-antibody.

The invention is illustrated by the following examples.

EXAMPLES

Example 1

Identification of CSFV specific cytotoxic T lymphocytes

Peripheral blood leukocytes were isolated from inbred miniature swine of MHC$^{d/d}$ haplotype after immunization with CSFV-strain Riems ($4 \cdot 10^5$ TCID$_{50}$ i.m.) following repeated challenges with $2 \cdot 10^7$ TCID$_{50}$ CSFV-strain Alfort and a final challenge with 3 ml intranasally of a serum ($1 \cdot 10^5$ TCID$_{50}$) obtained from a CSFV-strain Brescia infected pig. The cells were seeded in 96-well round bottom microtiter plates at a concentration of $1$–$2 \cdot 10^5$ cells per microculture in RPMI medium (10% FCS) and simultaneously restimulated with infectious virus ($5 \cdot 10^5$ TCID$_{50}$/ml CSFV-Alfort) for 3 to 5 days.

Culturing of infected target cells was done in the following way: from a miniature swine ("NIH-Minipig"; MHC$^{d/d}$ haplotype) a kidney was removed and cut to pieces under sterile conditions. The organ pieces were rinsed with PBS and 30–100 pieces were pipetted in a culture flask (25 cm$^2$). They were incubated in culture medium (10% FCS) to which a collagenase-dispase solution (stocksolution of 2.5 mg/ml diluted 1:6 in medium) was added. The cells were rinsed from the tissue with PBS, pelleted (6 min, 750 g) and washed twice in PBS. They were cultivated in DMEM (10% FCS) in culture flasks (25 and 75 cm$^2$).

For obtaining a stable, transformed cell line of target cells the kidney cells were transformed with a plasmid having the sequence for the "large T" antigen of SV-40) (Southern, P. and Berg, P., *J. Molec. Appl. Genetics.*, 1, 327–341, 1982; Fanning, E., *J. Viral.*, 66, 1289–1293, 1992). For this purified SV-40 plasmid pSV-3 neo (from Dr. T. C. Mettenleiter, BFAV Tübingen) was mixed with lipofectin to a DNA-lipofectin ratio of 1:4 and incubated for 15 min at room temperature. Of a largely (80%) confluent kidney cell culture the culture medium was removed and 2 ml OptiMEM-Medium (Gibco) was added. The lipofectin/DNA suspension was then added dropwise and the culture was initially incubated for 12 hours at 37° C. Then the medium was replaced by cloning medium (DMEM, F10(Gibco) and F12(Gibco) in a 2:1:1 ratio) with 10% FCS (foetal calf serum) and cultivated at 37° C. The MAX-cells thus obtained were selected by culturing with a neomycin analogon G418 (Boehringer) and tested for mycoplasma contamination (Mycoplasma Detection Kit, Boehringer Mannheim).

$1 \cdot 10^6$ target cells were infected with CSFV-Alfort at a m.o.i. of 0.5. 48 hours after infection the cells were trypsinated and collected in a 200 µl CTL assay medium (RPMI 1640 (Gibco), 3% FCS). The target cells were labelled with 100 µCi of Na$_2$$^{51}$CrO$_4$ for 90 min., washed three times and resuspended in CTL assay medium at a final concentration of $1 \cdot 10^4$ cells/ml.

Effector cells were diluted to achieve different effector-:target ratios and were added to triplicate wells in 100 µl volumes. $1 \cdot 10^3$/well target cells were added to the effector cells. The plates were centrifuged at 100 g for 5 minutes and incubated for 4 hours at 37° C. After centrifugation at 600 g for 10 minutes, 100 µl each supernatant were collected and the chromium release determined as cpm in a gamma radiation counter. Percent specific lysis was calculated by the formula:

$$\% \text{ specific lysis} = \frac{(\text{exp. cpm} - \text{spont. cpm}) * 100}{(\text{total cpm} - \text{spont. cpm})}$$

Target cell controls were included in the following way: in order to measure spontaneous radioisotope release (spont. cpm), target cells were incubated without effectors. In addition, the total chromium incorporation in target cells was determined (total cpm).

Results

Lysis of CSFV-infected target cells by cytotoxic T lymphocytes was higher than in the control group (FIG. 1). A more thar. 30% higher specific lysis was reached with a relatively low effector to target cell ratio (12:1), indicating a high rate of CSFV specific cytotoxic T lymphocytes.

Example 2

Cytotoxic T lymphocytes mediated lysis of target cells expressing truncated proteins $1 \cdot 10^6$ MAX cells (obtained as described in Example 1) were infected with different Vaccinia virus/CSFV recombinants at a multiplicity of infection of 2.0 for 16 hours. FIG. 2 shows the relative positions of the proteins of CSFV and the identification of the Vaccinia virus/CSFV recombinants obtained.

Cells which showed a moderate cytopathic effect, were trypsinated and collected in 200 µl CTL assay medium. The target cells were labelled with 100 µCi of $Na_2^{51}CrO_4$ for 90 min, washed three times and resuspended in CTL assay medium at a concentration of $1 \cdot 10^4$ cells/ml prior to use in the assay.

The assay was conducted in the same way as described in Example 1.

Results

The results of the chromium release assays indicated that CSFV-specific CTL recognize only target cells infected with the Vaccinia virus/p125S recombinant. Surprisingly, neither target cells expressing viral structural proteins nor cells expressing the autoprotease were lysed by the specific cytotoxic T lymphocytes (FIG. 3).

From the peptide products produced by the Vaccinia virus/p125S recombinant it seems that the 80 kD subunit or the p10 protein are responsible for the recognition (FIG. 4, panel B). Narrowing down this area it appears that Vaccinia virus/CSFV recombinant p80/VZ still shows specific lysis, while p80/VA and p80/VX are ineffective. This means (see FIG. 2; the nucleotide positions refer to the sequence of CSFV Alfort shown by Meyers et al., Virology 171, 555–567, 1989) that the T cell specific epitope is situated near the cleavage site between p125 and p10. The region identified as the region in which the epitope is harboured (the region still present in the recombinant p80/VZ and not present in p80/VA and p80/VX) is situated from amino acid position 2223 to 2285 (according to the sequence of CSFV Alfort (Meyers et al. supra), i.e. amino acid positions 1093 to 1155 of SEQ ID NO:2). Data obtained by N-terminal protein sequencing or p10 of BVDV-strain cp7 reveal that the cleavage site between p125 and p10 of CSFV-Alfort is located between amino acid positions 2272 and 2273 of CSFV-Alfort, i.e. between nucleotide positions 3426 and 3427 of SEQ ID NO:1.

Example 3

Identification of a T cell epitope recognized by CSFV-specific CTL

To determine the epitope recognized by virus specific CTL, nonapeptides and pentadecapeptides were synthesized overlapping by 8 and 12 amino acids, respectively, covering the amino acid region from positions 1093 to 1155 of SEQ ID NO:2.

$1 \cdot 10^6$ target cells were labelled with 100 µCi of $Na_2^{51}CrO_4$ for 90 min, washed three times and resuspended in CTL assay medium at a final concentration of $2 \cdot 10^4$ cells/ml. 50 µl of target cell suspension was added to triplicate wells of 96 well round bottom plates. The target cells were loaded with peptide by incubation with 100 µl peptide solution (5 mg/ml stock solution in DMSO; 1:4000 to 1:5000 diluted in RPMI medium, resulting in approximately 50 to 125 ng/$10^3$ target cells) for 1 hour. $1 \cdot 10^5$ effector cells were added to each well in 50 µl volumes to achieve an effector to target cell ratio of 100:1.

Chromium release assay was done in a way similar to Example 1 and 2.

Results

Specific lysis of target cells loaded with different peptides is shown in FIGS. 5 and 6. In FIG. 5 it is shown that the nonapeptide E-N-A-L-L-V-A-L-F (SEQ ID NO:6) causes the largest percentage of specific lysis, while in FIG. 6 the pentadecapapetide S-T-A-E-N-A-L-L-V-A-L-F-G-Y-V (SEQ ID NO:4) resulted in a significantly higher lysis of target cells compared to the target cells incubated with other pentadecapeptides. This pentadecapapetide contains the sequence of the nonapeptide identified already in FIG. 5. Nevertheless, CTL lysed target cells loaded with the nonapeptide more efficiently than target cells loaded with the pentadecamer, suggesting that nonapeptides have a higher affinity to porcine MHC-I molecules than pentadecapeptides.

Example 4

Crossreactivity of CSFV-specific CTL

Experiments regarding the crossreactivity of CSFV-specific CTL were performed using target cells infected with different CSFV-strains at a m.o.i. of 0.5 for 48 hours (performed in accordance to Example 1) or infected with the Vaccinia virus recombinants at a m.o.i. of 2.0 for 16 hours (performed in accordance to Example 2). The Vaccinia virus recombinants contained the coding sequences for the nonstructural proteins p125, p10 and the N-terminal part of p30 of CSFV-Alfort Tübingen (Vac-p125S) or the corresponding proteins of BVDV strain cp7 (Vac-p125S). The CTL activity of CSFV-sensitized effector cells was determined in chromium release assays using the infected MAX cells as targets.

For control non-infected and vaccinia virus wildtype (Vac-WR) infected targets were used.

Results

The results of both the experiments with CSFV-strains and with vaccinia virus recombinants are depicted in Table I. From these results it can be seen that CSFV specific CTL were capable of lysing target cells infected with different CSFV-strains. It is also shown that CSFV specific CTL were capable of lysing target cells expressing nonstructural proteins of a BVDV-strain, thereby suggesting that these nonstructural proteins harbour a T cell specific epitope which may be conserved for pestiviruses.

TABLE I

Cross-reactivity of CSFV-specific CTL.

| CSFV-strains | E:T ratio | |
|---|---|---|
| | 50:1 | 25:1 |
| Alfort Tübingen | 49% | 24% |
| Alfort 187 | 49% | 38% |
| Eystrup | 52% | 27% |
| Riems | 32% | 16% |
| Brescia | 27% | 14% |
| Schweinfurt | 42% | 23% |
| non-infected | 1% | 0% |

| Vaccinia virus | E:T ratio | |
|---|---|---|
| recombinants | 25:1 | 12:1 |
| Vac-p125S (CSFV) | 31% | 19% |
| Vac-p120S (BVDV) | 35% | 20% |
| Vac-WR | 18% | 7% |

BRIEF DESCRIPTION OF THE DRAWINGS

FIGS. 4(A–F): CTL mediated lysis of target cells expressing truncated nonstructural proteins. Presentation of data analog to FIG. 3.

FIG. 5: Lysis of peptide target cells by CSFV-specific CTL. Radiolabelled MAX-cells were incubated with different nonapeptides. The bars indicate percent specific lysis by an effector to target ratio of 100 to 1. Controls: specific lysis of CSFV-infected and non-infected target cells.

SEQUENCE LISTING

Figure 1:
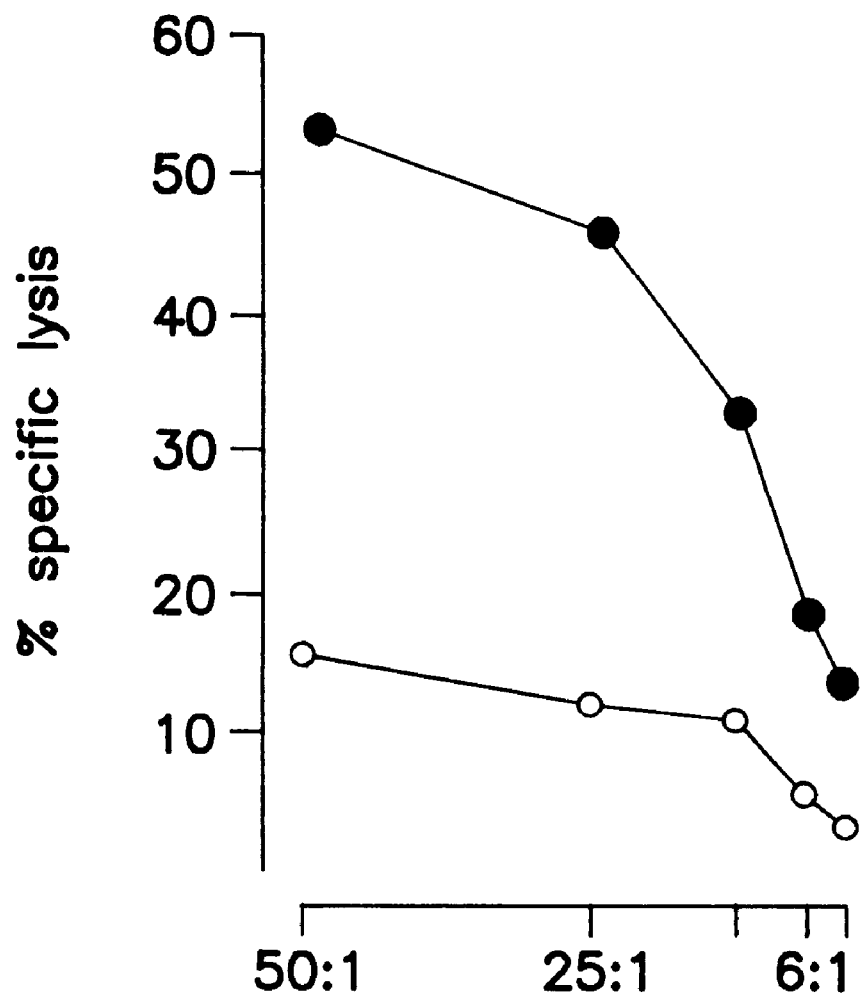
FIG. 1: Results of chromium release assay indicating CSFV specific lysis of target cells by cytotoxic T cells. Open circles indicate non infected control target cells, full circles indicate CSFV infected target cells. The % specific lysis is indicated on the Y-axis, while the X-axis shows the ratio of effector to target cells.
Figure 2:
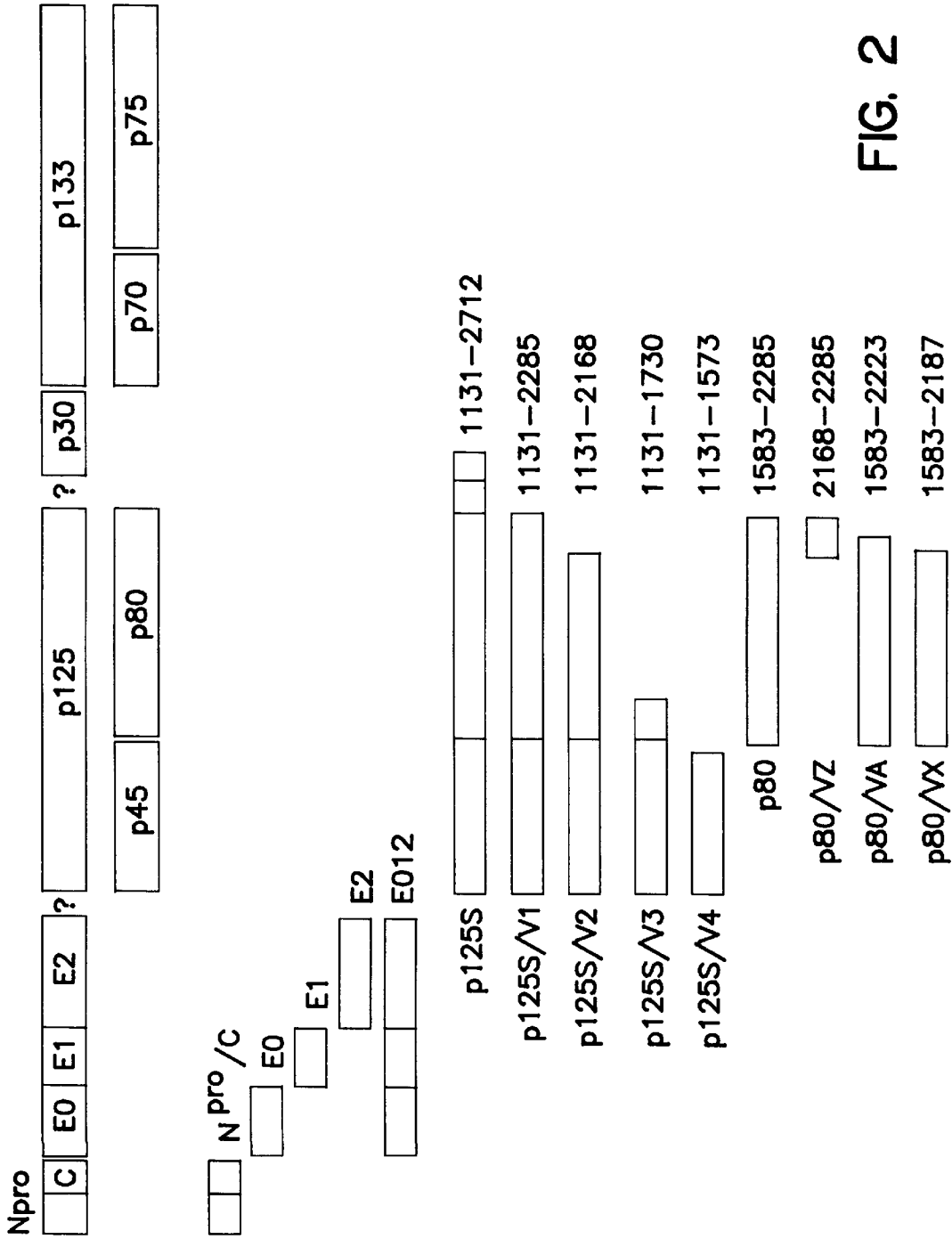
FIG. 2: Vaccinia virus/CSFV recombinants used for infection of autologous target cells. The relative positions of the N-terminal autoprotease (Npro), the structural proteins core (C), E0, E1, E2 and the nonstructural proteins p125, p30 and p133 on the CSFV polyprotein as well as their processing products are indicated. In addition, the viral proteins and truncated p125-proteins expressed as Vaccinia virus/CSFV recombinants are shown. The amino acid positions indicated are in accordance to the sequence of CSFV-Alfort.
Figure 3:
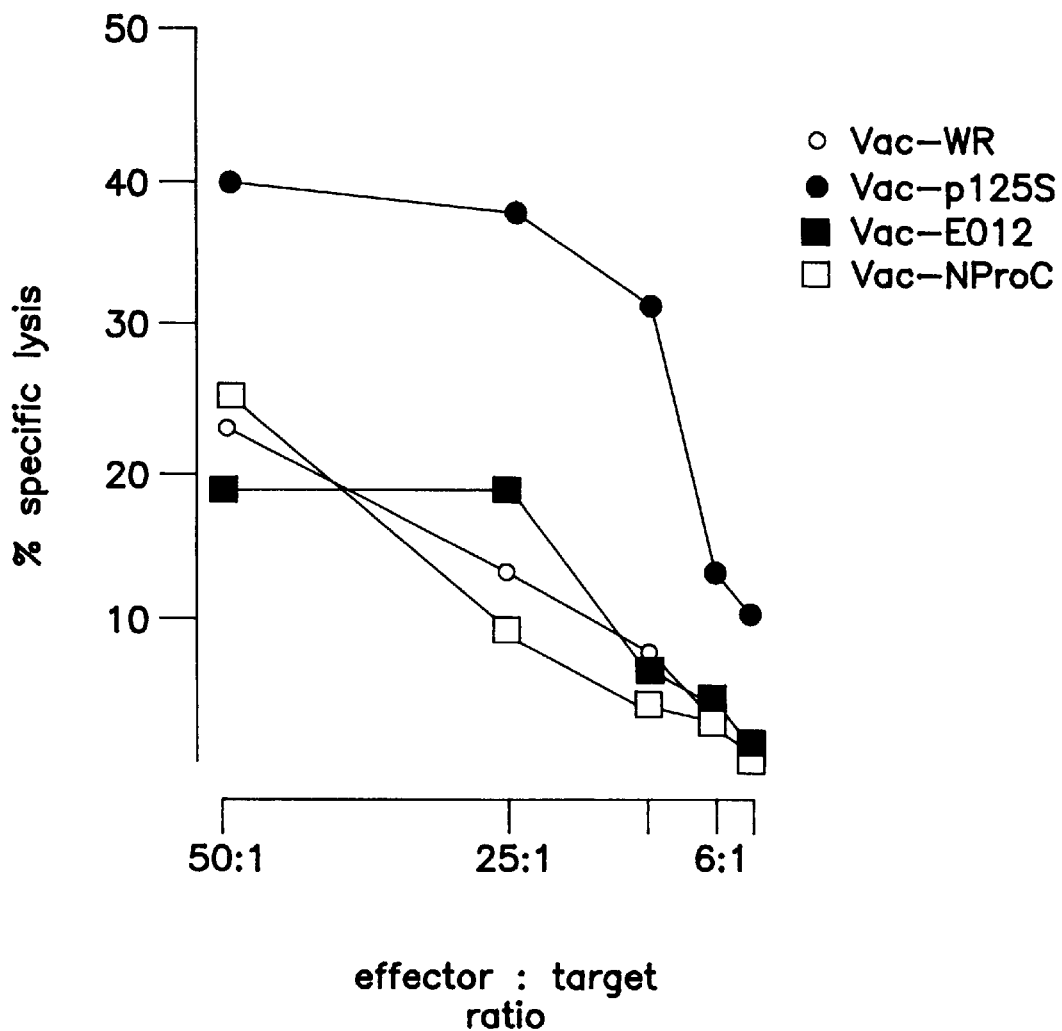
FIG. 3: CTL mediated lysis of target cells infected with different Vaccinia virus/CSFV recombinants. MAX-cells were infected with Vaccinia virus wildtype (Vacc-WR, open circles) and the Vaccinia virus/CSF7 recombinants Vacc-$N^{pro}C$ (open squares), Vacc-E012 (closed squares) or Vacc-p125S (closed circles) and used as target cells in chromium release assays against CSFV-specific CTL. Axes identical to FIG. 1.
Figure 6:
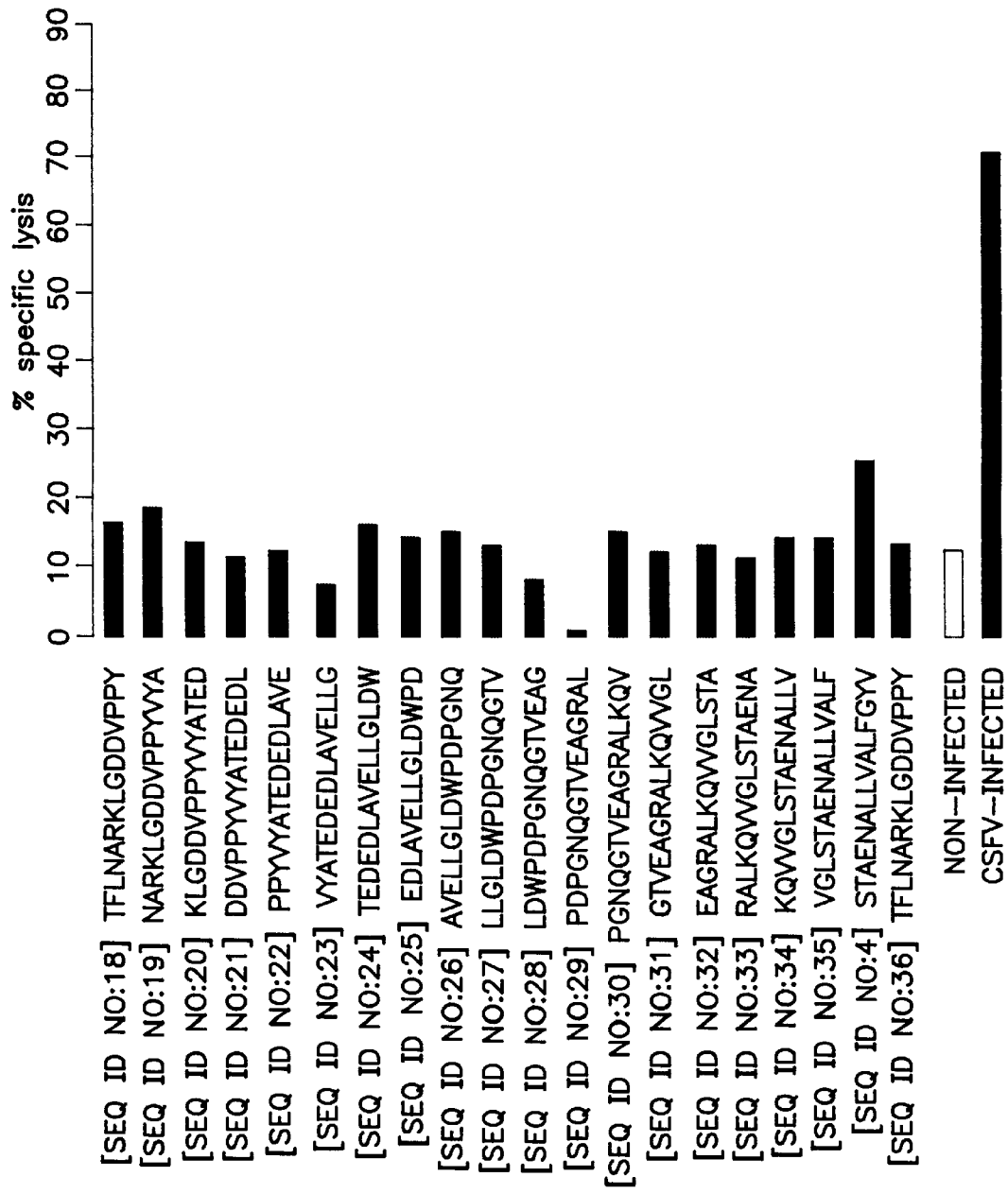
FIG. 6: Lysis of pentadecapeptide loaded target cells. Legends as in FIG. 5.

```
<160> NUMBER OF SEQ ID NOS: 36

<210> SEQ ID NO 1
<211> LENGTH: 3639
<212> TYPE: DNA
<213> ORGANISM: Classical Swine Fever Virus
<220> FEATURE:
<221> NAME/KEY: CDS
<222> LOCATION: (1)..(3639)

<400> SEQUENCE: 1 aag ggt ggt aag ata gat ggt ggc tgg cag aga caa ccg gtg acc agt      48
Lys Gly Gly Lys Ile Asp Gly Gly Trp Gln Arg Gln Pro Val Thr Ser
  1               5                  10                  15 ttt gac atc caa ctc gca ctg gca gtc gta gta gtc gtt gtg atg ttg      96
Phe Asp Ile Gln Leu Ala Leu Ala Val Val Val Val Val Val Met Leu
                 20                  25                  30 ctg gca aag aga gac ccg act act ttc cct ttg gta atc aca gtg gca     144
Leu Ala Lys Arg Asp Pro Thr Thr Phe Pro Leu Val Ile Thr Val Ala
             35                  40                  45 acc ctg aga acg gcc aag ata acc aac ggt ttt agc aca gat cta gtc     192
Thr Leu Arg Thr Ala Lys Ile Thr Asn Gly Phe Ser Thr Asp Leu Val
         50                  55                  60 ata gcc aca gtg tcg gca gct ttg tta act tgg acc tat atc agc gac     240
Ile Ala Thr Val Ser Ala Ala Leu Leu Thr Trp Thr Tyr Ile Ser Asp
 65                  70                  75                  80 tac tac aaa tac aag act tgg cta cag tac ctc gtc agc acg gtg act     288
Tyr Tyr Lys Tyr Lys Thr Trp Leu Gln Tyr Leu Val Ser Thr Val Thr
                 85                  90                  95 gga atc ttc ctg ata agg gtg ctg aag gga ata ggc gaa ttg gat ctg     336
Gly Ile Phe Leu Ile Arg Val Leu Lys Gly Ile Gly Glu Leu Asp Leu
                100                 105                 110
```

```
cac gcc cca acc ttg ccg tct cac aga ccc ctc ttt tac atc ctt gta      384
His Ala Pro Thr Leu Pro Ser His Arg Pro Leu Phe Tyr Ile Leu Val
        115                 120                 125 tac ctt att tcc act gcc gtg gta act aga tgg aat ctg gac gta gcc      432
Tyr Leu Ile Ser Thr Ala Val Val Thr Arg Trp Asn Leu Asp Val Ala
    130                 135                 140 gga ttg ttg ctg cag tgc gtc cca act ctt tta atg gtt ttt acg atg      480
Gly Leu Leu Leu Gln Cys Val Pro Thr Leu Leu Met Val Phe Thr Met
145                 150                 155                 160 tgg gca gac att ctc acc cta att ctc ata cta cct act tat gag tta      528
Trp Ala Asp Ile Leu Thr Leu Ile Leu Ile Leu Pro Thr Tyr Glu Leu
                165                 170                 175 aca aag tta tac tac ctt aag gaa gtg aag att ggg gca gaa aga ggt      576
Thr Lys Leu Tyr Tyr Leu Lys Glu Val Lys Ile Gly Ala Glu Arg Gly
            180                 185                 190 tgg ctg tgg aaa act aac tat aag agg gta aac gac atc tac gag gtc      624
Trp Leu Trp Lys Thr Asn Tyr Lys Arg Val Asn Asp Ile Tyr Glu Val
        195                 200                 205 gac caa act agc gaa ggg gtt tac ctt ttc cct tct aaa cag agg acg      672
Asp Gln Thr Ser Glu Gly Val Tyr Leu Phe Pro Ser Lys Gln Arg Thr
    210                 215                 220 agc gct ata act agt acc atg ttg cca tta atc aaa gcc ata ctc att      720
Ser Ala Ile Thr Ser Thr Met Leu Pro Leu Ile Lys Ala Ile Leu Ile
225                 230                 235                 240 agc tgc atc agc aac aag tgg caa ctc ata tac tta ctg tac ttg ata      768
Ser Cys Ile Ser Asn Lys Trp Gln Leu Ile Tyr Leu Leu Tyr Leu Ile
                245                 250                 255 ttt gaa gtg tct tac tac ctc cac aag aaa gtt ata gat gaa ata gct      816
Phe Glu Val Ser Tyr Tyr Leu His Lys Lys Val Ile Asp Glu Ile Ala
            260                 265                 270 ggt ggg acc aac ttc gtt tca agg ctc gtg gcg gct ttg att gaa gtc      864
Gly Gly Thr Asn Phe Val Ser Arg Leu Val Ala Ala Leu Ile Glu Val
        275                 280                 285 aat tgg gcc ttc gac aat gaa gaa gtc aaa ggc tta aag aag ttc ttc      912
Asn Trp Ala Phe Asp Asn Glu Glu Val Lys Gly Leu Lys Lys Phe Phe
    290                 295                 300 ttg ctg tct agt agg gtc aaa gag ttg atc atc aaa cac aaa gtg agg      960
Leu Leu Ser Ser Arg Val Lys Glu Leu Ile Ile Lys His Lys Val Arg
305                 310                 315                 320 aat gaa gta gtg gtc cgc tgg ttt gga gat gaa gag att tat ggg atg     1008
Asn Glu Val Val Val Arg Trp Phe Gly Asp Glu Glu Ile Tyr Gly Met
                325                 330                 335 cca aag ctg atc ggc tta gtt aag gca gca aca cta agt aga aac aaa     1056
Pro Lys Leu Ile Gly Leu Val Lys Ala Ala Thr Leu Ser Arg Asn Lys
            340                 345                 350 cac tgt atg ttg tgt acc gtc tgt gag gac aga gat tgg aga ggg gaa     1104
His Cys Met Leu Cys Thr Val Cys Glu Asp Arg Asp Trp Arg Gly Glu
        355                 360                 365 act tgc cct aaa tgt ggg cgt ttt gga cca cca gtg gtc tgc ggt atg     1152
Thr Cys Pro Lys Cys Gly Arg Phe Gly Pro Pro Val Val Cys Gly Met
    370                 375                 380 acc cta gcc gat ttc gaa gaa aaa cac tat aaa agg att ttc att aga     1200
Thr Leu Ala Asp Phe Glu Glu Lys His Tyr Lys Arg Ile Phe Ile Arg
385                 390                 395                 400 gag gac caa tca ggc ggg cca ctt agg gag gag cat gca ggg tac ttg     1248
Glu Asp Gln Ser Gly Gly Pro Leu Arg Glu Glu His Ala Gly Tyr Leu
                405                 410                 415 cag tac aaa gcc agg ggt caa ctg ttt ttg agg aac ctc cca gtg tta     1296
Gln Tyr Lys Ala Arg Gly Gln Leu Phe Leu Arg Asn Leu Pro Val Leu
            420                 425                 430
```

-continued

| | | |
|---|---|---|
| gct aca aaa gtc aag atg ctc ctg gtt ggt aac ctc ggg aca gag att<br>Ala Thr Lys Val Lys Met Leu Leu Val Gly Asn Leu Gly Thr Glu Ile<br>435                    440                    445 | 1344 |
| ggg gat ctg gaa cac ctt ggc tgg gtg ctt aga ggg cca gct gtt tgc<br>Gly Asp Leu Glu His Leu Gly Trp Val Leu Arg Gly Pro Ala Val Cys<br>450                    455                    460 | 1392 |
| aag aag gtt act gaa cac gaa aga tgc acc acg tct ata atg gat aag<br>Lys Lys Val Thr Glu His Glu Arg Cys Thr Thr Ser Ile Met Asp Lys<br>465                    470                    475                    480 | 1440 |
| ttg act gct ttc ttt gga gta atg cca agg ggc act act ccc aga gct<br>Leu Thr Ala Phe Phe Gly Val Met Pro Arg Gly Thr Thr Pro Arg Ala<br>                    485                    490                    495 | 1488 |
| ccc gta aga ttc cct acc tcc ctc cta aag ata aga aga ggg ctg gag<br>Pro Val Arg Phe Pro Thr Ser Leu Leu Lys Ile Arg Arg Gly Leu Glu<br>500                    505                    510 | 1536 |
| act ggt tgg gct tac aca cac caa ggt ggc atc agc tca gta gac cat<br>Thr Gly Trp Ala Tyr Thr His Gln Gly Gly Ile Ser Ser Val Asp His<br>                    515                    520                    525 | 1584 |
| gtc act tgt ggg aaa gac tta ctg gtg tgt gac acc atg ggt cgg aca<br>Val Thr Cys Gly Lys Asp Leu Leu Val Cys Asp Thr Met Gly Arg Thr<br>530                    535                    540 | 1632 |
| agg gtt gtt tgc cag tca aat aat aag atg acc gac gag tcc gaa tac<br>Arg Val Val Cys Gln Ser Asn Asn Lys Met Thr Asp Glu Ser Glu Tyr<br>545                    550                    555                    560 | 1680 |
| gga gtc aaa act gac tcc ggg tgc cca gag gga gcc agg tgt tac gtg<br>Gly Val Lys Thr Asp Ser Gly Cys Pro Glu Gly Ala Arg Cys Tyr Val<br>                    565                    570                    575 | 1728 |
| ttt aac ccg gaa gca gtt aac ata tca ggc act aaa gga gcc atg gtc<br>Phe Asn Pro Glu Ala Val Asn Ile Ser Gly Thr Lys Gly Ala Met Val<br>580                    585                    590 | 1776 |
| cac tta cag aaa acg ggt gga gaa ttc acc tgt gtg aca gca tca gga<br>His Leu Gln Lys Thr Gly Gly Glu Phe Thr Cys Val Thr Ala Ser Gly<br>                    595                    600                    605 | 1824 |
| acc ccg gcc ttc ttt gac ctc aag aac ctt aag ggc tgg tca ggg cta<br>Thr Pro Ala Phe Phe Asp Leu Lys Asn Leu Lys Gly Trp Ser Gly Leu<br>610                    615                    620 | 1872 |
| ccg ata ttt gaa gca tca agt gga agg gta gtc gga agg gtc aag gtc<br>Pro Ile Phe Glu Ala Ser Ser Gly Arg Val Val Gly Arg Val Lys Val<br>625                    630                    635                    640 | 1920 |
| ggg aag aac gag gat tcc aaa cca acc aag ctc atg agt ggg ata caa<br>Gly Lys Asn Glu Asp Ser Lys Pro Thr Lys Leu Met Ser Gly Ile Gln<br>                    645                    650                    655 | 1968 |
| acg gtt tct aaa agc gcc aca gac ttg acg gag atg gtg aag aag ata<br>Thr Val Ser Lys Ser Ala Thr Asp Leu Thr Glu Met Val Lys Lys Ile<br>660                    665                    670 | 2016 |
| acg acc atg aac agg gga gag ttc aga caa ata acc ctg gcc aca ggt<br>Thr Thr Met Asn Arg Gly Glu Phe Arg Gln Ile Thr Leu Ala Thr Gly<br>                    675                    680                    685 | 2064 |
| gcc gga aaa act aca gag ctc cct aga tca gtt ata gaa gag ata ggg<br>Ala Gly Lys Thr Thr Glu Leu Pro Arg Ser Val Ile Glu Glu Ile Gly<br>690                    695                    700 | 2112 |
| agg cat aag agg gtg ttg gtc tta atc ccc ttg agg gcg gca gca gaa<br>Arg His Lys Arg Val Leu Val Leu Ile Pro Leu Arg Ala Ala Ala Glu<br>705                    710                    715                    720 | 2160 |
| tca gta tac caa tac atg aga cag aaa cat ccg agt ata gca ttc aat<br>Ser Val Tyr Gln Tyr Met Arg Gln Lys His Pro Ser Ile Ala Phe Asn<br>                    725                    730                    735 | 2208 |
| cta agg ata ggt gag atg aag gaa ggt gat atg gcc acg gga ata acc<br>Leu Arg Ile Gly Glu Met Lys Glu Gly Asp Met Ala Thr Gly Ile Thr<br>740                    745                    750 | 2256 |

-continued

| | |
|---|---|
| tat gcc tct tac ggt tac ttt tgc cag atg tca caa ccc aag ctg aga<br>Tyr Ala Ser Tyr Gly Tyr Phe Cys Gln Met Ser Gln Pro Lys Leu Arg<br>        755                      760                      765 | 2304 |
| gcc gca atg gta gaa tat tcc ttt ata ttc cta gat gag tat cat tgt<br>Ala Ala Met Val Glu Tyr Ser Phe Ile Phe Leu Asp Glu Tyr His Cys<br>770                      775                      780 | 2352 |
| gct acc cca gaa caa ctg gca atc atg ggg aag atc cac aga ttc tca<br>Ala Thr Pro Glu Gln Leu Ala Ile Met Gly Lys Ile His Arg Phe Ser<br>785                      790                      795                      800 | 2400 |
| gaa aac ctg cgg gtg gta gct atg aca gcg aca ccg gca ggc aca gta<br>Glu Asn Leu Arg Val Val Ala Met Thr Ala Thr Pro Ala Gly Thr Val<br>                      805                      810                      815 | 2448 |
| aca acc act ggg cag aaa cac cct ata gag gaa ttt ata gcc ccg gaa<br>Thr Thr Thr Gly Gln Lys His Pro Ile Glu Glu Phe Ile Ala Pro Glu<br>        820                      825                      830 | 2496 |
| gtg atg aaa gga gaa gac ttg ggt tct gag tac tta gat att gcc gga<br>Val Met Lys Gly Glu Asp Leu Gly Ser Glu Tyr Leu Asp Ile Ala Gly<br>                835                      840                      845 | 2544 |
| ctg aag ata cca gta gag gag atg aag aat aac atg cta gtt ttt gtg<br>Leu Lys Ile Pro Val Glu Glu Met Lys Asn Asn Met Leu Val Phe Val<br>850                      855                      860 | 2592 |
| ccc acc agg aac atg gcg gta gag gcg gca aag aaa ttg aag gcc aaa<br>Pro Thr Arg Asn Met Ala Val Glu Ala Ala Lys Lys Leu Lys Ala Lys<br>865                      870                      875                      880 | 2640 |
| gga tac aac tcg ggc tac tac tac agc gga gag gac cca tct aac ctg<br>Gly Tyr Asn Ser Gly Tyr Tyr Tyr Ser Gly Glu Asp Pro Ser Asn Leu<br>                885                      890                      895 | 2688 |
| agg gtg gtg acg tcg cag tcc cca tac gtg gtg gta gca acc aac gca<br>Arg Val Val Thr Ser Gln Ser Pro Tyr Val Val Val Ala Thr Asn Ala<br>        900                      905                      910 | 2736 |
| ata gaa tcg ggc gtt acc ctc ccg gac ctg gac gtg gtt gtc gac acg<br>Ile Glu Ser Gly Val Thr Leu Pro Asp Leu Asp Val Val Val Asp Thr<br>                915                      920                      925 | 2784 |
| gga ctc aag tgt gaa aaa aga atc cga ctg tca ccc aag atg cct ttc<br>Gly Leu Lys Cys Glu Lys Arg Ile Arg Leu Ser Pro Lys Met Pro Phe<br>930                      935                      940 | 2832 |
| ata gtg acg ggc ctg aaa aga atg gcc gtc act att ggg gaa caa gcc<br>Ile Val Thr Gly Leu Lys Arg Met Ala Val Thr Ile Gly Glu Gln Ala<br>945                      950                      955                      960 | 2880 |
| cag aga aga ggg agg gtt gga aga gtg aag ccc ggg aga tac tac agg<br>Gln Arg Arg Gly Arg Val Gly Arg Val Lys Pro Gly Arg Tyr Tyr Arg<br>                      965                      970                      975 | 2928 |
| agt caa gaa aca cct gtc ggc tct aaa gac tac cat tat gac tta ttg<br>Ser Gln Glu Thr Pro Val Gly Ser Lys Asp Tyr His Tyr Asp Leu Leu<br>        980                      985                      990 | 2976 |
| caa gcc cag agg tac ggc ata gaa gat ggg ata aat atc acc aaa tcc<br>Gln Ala Gln Arg Tyr Gly Ile Glu Asp Gly Ile Asn Ile Thr Lys Ser<br>                995                      1000                     1005 | 3024 |
| ttc aga gag atg aac tac gac tgg agc ctt tat gag gaa gat agc ctg<br>Phe Arg Glu Met Asn Tyr Asp Trp Ser Leu Tyr Glu Glu Asp Ser Leu<br>1010                      1015                     1020 | 3072 |
| atg atc aca caa ctg gaa atc ctc aac aac ctg ttg ata tca gaa gag<br>Met Ile Thr Gln Leu Glu Ile Leu Asn Asn Leu Leu Ile Ser Glu Glu<br>1025                      1030                     1035                     1040 | 3120 |
| ctg ccg atg gca gta aaa aat ata atg gcc agg acc gac cac cca gaa<br>Leu Pro Met Ala Val Lys Asn Ile Met Ala Arg Thr Asp His Pro Glu<br>                      1045                     1050                     1055 | 3168 |
| cca att caa ctc gcg tat aac agc tac gag aca cag gtg ccg gta tta<br>Pro Ile Gln Leu Ala Tyr Asn Ser Tyr Glu Thr Gln Val Pro Val Leu<br>                1060                     1065                     1070 | 3216 |

-continued

```
ttc cca aaa ata aga aat gga gag gtg act gat act tac gat aat tac    3264
Phe Pro Lys Ile Arg Asn Gly Glu Val Thr Asp Thr Tyr Asp Asn Tyr
    1075                1080                1085 acc ttc ctc aat gca aga aaa ttg gga gat gac gta ccc ccc tac gtg    3312
Thr Phe Leu Asn Ala Arg Lys Leu Gly Asp Asp Val Pro Pro Tyr Val
1090                1095                1100 tat gct aca gag gat gag gac ttg gca gtg gaa ctg ttg ggc cta gat    3360
Tyr Ala Thr Glu Asp Glu Asp Leu Ala Val Glu Leu Leu Gly Leu Asp
1105                1110                1115                1120 tgg ccg gac cca gga aac caa ggc acc gtg gaa gct ggc aga gca cta    3408
Trp Pro Asp Pro Gly Asn Gln Gly Thr Val Glu Ala Gly Arg Ala Leu
                1125                1130                1135 aaa cag gtg gtt ggt cta tca aca gca gag aac gcc ctg cta gtc gcc    3456
Lys Gln Val Val Gly Leu Ser Thr Ala Glu Asn Ala Leu Leu Val Ala
            1140                1145                1150 ctg ttc ggc tac gtg ggg tac cag gcg ctt tca aag aga cat ata cca    3504
Leu Phe Gly Tyr Val Gly Tyr Gln Ala Leu Ser Lys Arg His Ile Pro
        1155                1160                1165 ctg gtc aca gat ata tat tca gta gaa gat cac agg cta gag gac act    3552
Leu Val Thr Asp Ile Tyr Ser Val Glu Asp His Arg Leu Glu Asp Thr
    1170                1175                1180 acg cac cta cag tat gct ccg aat gcc atc aag acg gag ggg aag gaa    3600
Thr His Leu Gln Tyr Ala Pro Asn Ala Ile Lys Thr Glu Gly Lys Glu
1185                1190                1195                1200 act gaa ttg aag gag ctg gct cag ggg gat gtg cag aga                3639
Thr Glu Leu Lys Glu Leu Ala Gln Gly Asp Val Gln Arg
                1205                1210

<210> SEQ ID NO 2
<211> LENGTH: 1213
<212> TYPE: PRT
<213> ORGANISM: Classical Swine Fever Virus

<400> SEQUENCE: 2

Lys Gly Gly Lys Ile Asp Gly Gly Trp Gln Arg Gln Pro Val Thr Ser
 1               5                  10                  15

Phe Asp Ile Gln Leu Ala Leu Ala Val Val Val Val Val Met Leu
                20                  25                  30

Leu Ala Lys Arg Asp Pro Thr Thr Phe Pro Leu Val Ile Thr Val Ala
        35                  40                  45

Thr Leu Arg Thr Ala Lys Ile Thr Asn Gly Phe Ser Thr Asp Leu Val
    50                  55                  60

Ile Ala Thr Val Ser Ala Ala Leu Leu Thr Trp Thr Tyr Ile Ser Asp
65                  70                  75                  80

Tyr Tyr Lys Tyr Lys Thr Trp Leu Gln Tyr Leu Val Ser Thr Val Thr
                85                  90                  95

Gly Ile Phe Leu Ile Arg Val Leu Lys Gly Ile Gly Glu Leu Asp Leu
            100                 105                 110

His Ala Pro Thr Leu Pro Ser His Arg Pro Leu Phe Tyr Ile Leu Val
        115                 120                 125

Tyr Leu Ile Ser Thr Ala Val Val Thr Arg Trp Asn Leu Asp Val Ala
    130                 135                 140

Gly Leu Leu Leu Gln Cys Val Pro Thr Leu Leu Met Val Phe Thr Met
145                 150                 155                 160

Trp Ala Asp Ile Leu Thr Leu Ile Leu Ile Leu Pro Thr Tyr Glu Leu
                165                 170                 175

Thr Lys Leu Tyr Tyr Leu Lys Glu Val Lys Ile Gly Ala Glu Arg Gly
            180                 185                 190
```

```
Trp Leu Trp Lys Thr Asn Tyr Lys Arg Val Asn Asp Ile Tyr Glu Val
            195                 200                 205

Asp Gln Thr Ser Glu Gly Val Tyr Leu Phe Pro Ser Lys Gln Arg Thr
            210                 215                 220

Ser Ala Ile Thr Ser Thr Met Leu Pro Leu Ile Lys Ala Ile Leu Ile
225                 230                 235                 240

Ser Cys Ile Ser Asn Lys Trp Gln Leu Ile Tyr Leu Leu Tyr Leu Ile
                245                 250                 255

Phe Glu Val Ser Tyr Tyr Leu His Lys Lys Val Ile Asp Glu Ile Ala
                260                 265                 270

Gly Gly Thr Asn Phe Val Ser Arg Leu Val Ala Ala Leu Ile Glu Val
            275                 280                 285

Asn Trp Ala Phe Asp Asn Glu Val Lys Gly Leu Lys Lys Phe Phe
            290                 295                 300

Leu Leu Ser Ser Arg Val Lys Glu Leu Ile Ile Lys His Lys Val Arg
305                 310                 315                 320

Asn Glu Val Val Val Arg Trp Phe Gly Asp Glu Glu Ile Tyr Gly Met
                325                 330                 335

Pro Lys Leu Ile Gly Leu Val Lys Ala Ala Thr Leu Ser Arg Asn Lys
                340                 345                 350

His Cys Met Leu Cys Thr Val Cys Glu Asp Arg Asp Trp Arg Gly Glu
            355                 360                 365

Thr Cys Pro Lys Cys Gly Arg Phe Gly Pro Pro Val Val Cys Gly Met
370                 375                 380

Thr Leu Ala Asp Phe Glu Glu Lys His Tyr Lys Arg Ile Phe Ile Arg
385                 390                 395                 400

Glu Asp Gln Ser Gly Gly Pro Leu Arg Glu Glu His Ala Gly Tyr Leu
                405                 410                 415

Gln Tyr Lys Ala Arg Gly Gln Leu Phe Leu Arg Asn Leu Pro Val Leu
                420                 425                 430

Ala Thr Lys Val Lys Met Leu Leu Val Gly Asn Leu Gly Thr Glu Ile
                435                 440                 445

Gly Asp Leu Glu His Leu Gly Trp Val Leu Arg Gly Pro Ala Val Cys
450                 455                 460

Lys Lys Val Thr Glu His Glu Arg Cys Thr Thr Ser Ile Met Asp Lys
465                 470                 475                 480

Leu Thr Ala Phe Phe Gly Val Met Pro Arg Gly Thr Thr Pro Arg Ala
                485                 490                 495

Pro Val Arg Phe Pro Thr Ser Leu Leu Lys Ile Arg Arg Gly Leu Glu
                500                 505                 510

Thr Gly Trp Ala Tyr Thr His Gln Gly Gly Ile Ser Ser Val Asp His
            515                 520                 525

Val Thr Cys Gly Lys Asp Leu Leu Val Cys Asp Thr Met Gly Arg Thr
            530                 535                 540

Arg Val Val Cys Gln Ser Asn Asn Lys Met Thr Asp Glu Ser Glu Tyr
545                 550                 555                 560

Gly Val Lys Thr Asp Ser Gly Cys Pro Glu Gly Ala Arg Cys Tyr Val
                565                 570                 575

Phe Asn Pro Glu Ala Val Asn Ile Ser Gly Thr Lys Gly Ala Met Val
                580                 585                 590

His Leu Gln Lys Thr Gly Gly Glu Phe Thr Cys Val Thr Ala Ser Gly
                595                 600                 605

Thr Pro Ala Phe Phe Asp Leu Lys Asn Leu Lys Gly Trp Ser Gly Leu
```

-continued

```
            610                 615                 620
Pro Ile Phe Glu Ala Ser Ser Gly Arg Val Val Gly Arg Val Lys Val
625                 630                 635                 640

Gly Lys Asn Glu Asp Ser Lys Pro Thr Lys Leu Met Ser Gly Ile Gln
                    645                 650                 655

Thr Val Ser Lys Ser Ala Thr Asp Leu Thr Glu Met Val Lys Lys Ile
                660                 665                 670

Thr Thr Met Asn Arg Gly Glu Phe Arg Gln Ile Thr Leu Ala Thr Gly
            675                 680                 685

Ala Gly Lys Thr Thr Glu Leu Pro Arg Ser Val Ile Glu Glu Ile Gly
690                 695                 700

Arg His Lys Arg Val Leu Val Leu Ile Pro Leu Arg Ala Ala Ala Glu
705                 710                 715                 720

Ser Val Tyr Gln Tyr Met Arg Gln Lys His Pro Ser Ile Ala Phe Asn
                725                 730                 735

Leu Arg Ile Gly Glu Met Lys Glu Gly Asp Met Ala Thr Gly Ile Thr
                740                 745                 750

Tyr Ala Ser Tyr Gly Tyr Phe Cys Gln Met Ser Gln Pro Lys Leu Arg
            755                 760                 765

Ala Ala Met Val Glu Tyr Ser Phe Ile Phe Leu Asp Glu Tyr His Cys
770                 775                 780

Ala Thr Pro Glu Gln Leu Ala Ile Met Gly Lys Ile His Arg Phe Ser
785                 790                 795                 800

Glu Asn Leu Arg Val Val Ala Met Thr Ala Thr Pro Ala Gly Thr Val
                805                 810                 815

Thr Thr Thr Gly Gln Lys His Pro Ile Glu Glu Phe Ile Ala Pro Glu
            820                 825                 830

Val Met Lys Gly Glu Asp Leu Gly Ser Glu Tyr Leu Asp Ile Ala Gly
            835                 840                 845

Leu Lys Ile Pro Val Glu Glu Met Lys Asn Asn Met Leu Val Phe Val
850                 855                 860

Pro Thr Arg Asn Met Ala Val Glu Ala Ala Lys Lys Leu Lys Ala Lys
865                 870                 875                 880

Gly Tyr Asn Ser Gly Tyr Tyr Tyr Ser Gly Glu Asp Pro Ser Asn Leu
                885                 890                 895

Arg Val Val Thr Ser Gln Ser Pro Tyr Val Val Ala Thr Asn Ala
                900                 905                 910

Ile Glu Ser Gly Val Thr Leu Pro Asp Leu Asp Val Val Val Asp Thr
            915                 920                 925

Gly Leu Lys Cys Glu Lys Arg Ile Arg Leu Ser Pro Lys Met Pro Phe
930                 935                 940

Ile Val Thr Gly Leu Lys Arg Met Ala Val Thr Ile Gly Glu Gln Ala
945                 950                 955                 960

Gln Arg Arg Gly Arg Val Gly Arg Val Lys Pro Gly Arg Tyr Tyr Arg
                965                 970                 975

Ser Gln Glu Thr Pro Val Gly Ser Lys Asp Tyr His Tyr Asp Leu Leu
            980                 985                 990

Gln Ala Gln Arg Tyr Gly Ile Glu Asp Gly Ile Asn Ile Thr Lys Ser
            995                 1000                1005

Phe Arg Glu Met Asn Tyr Asp Trp Ser Leu Tyr Glu Glu Asp Ser Leu
    1010                1015                1020

Met Ile Thr Gln Leu Glu Ile Leu Asn Asn Leu Leu Ile Ser Glu Glu
1025                1030                1035                1040
```

```
Leu Pro Met Ala Val Lys Asn Ile Met Ala Arg Thr Asp His Pro Glu
            1045                1050                1055

Pro Ile Gln Leu Ala Tyr Asn Ser Tyr Glu Thr Gln Val Pro Val Leu
        1060                1065                1070

Phe Pro Lys Ile Arg Asn Gly Glu Val Thr Asp Thr Tyr Asp Asn Tyr
    1075                1080                1085

Thr Phe Leu Asn Ala Arg Lys Leu Gly Asp Asp Val Pro Pro Tyr Val
1090                1095                1100

Tyr Ala Thr Glu Asp Glu Asp Leu Ala Val Glu Leu Leu Gly Leu Asp
1105                1110                1115                1120

Trp Pro Asp Pro Gly Asn Gln Gly Thr Val Glu Ala Gly Arg Ala Leu
            1125                1130                1135

Lys Gln Val Val Gly Leu Ser Thr Ala Glu Asn Ala Leu Leu Val Ala
                1140                1145                1150

Leu Phe Gly Tyr Val Gly Tyr Gln Ala Leu Ser Lys Arg His Ile Pro
        1155                1160                1165

Leu Val Thr Asp Ile Tyr Ser Val Glu Asp His Arg Leu Glu Asp Thr
    1170                1175                1180

Thr His Leu Gln Tyr Ala Pro Asn Ala Ile Lys Thr Glu Gly Lys Glu
1185                1190                1195                1200

Thr Glu Leu Lys Glu Leu Ala Gln Gly Asp Val Gln Arg
            1205                1210

<210> SEQ ID NO 3
<211> LENGTH: 45
<212> TYPE: DNA
<213> ORGANISM: Classical Swine Fever Virus
<220> FEATURE:
<221> NAME/KEY: CDS
<222> LOCATION: (1)..(45)

<400> SEQUENCE: 3 tca aca gca gag aac gcc ctg cta gtc gcc ctg ttc ggc tac gtg         45
Ser Thr Ala Glu Asn Ala Leu Leu Val Ala Leu Phe Gly Tyr Val
  1               5                  10                  15

<210> SEQ ID NO 4
<211> LENGTH: 15
<212> TYPE: PRT
<213> ORGANISM: Classical Swine Fever Virus

<400> SEQUENCE: 4

Ser Thr Ala Glu Asn Ala Leu Leu Val Ala Leu Phe Gly Tyr Val
  1               5                  10                  15

<210> SEQ ID NO 5
<211> LENGTH: 27
<212> TYPE: DNA
<213> ORGANISM: Classical Swine Fever Virus
<220> FEATURE:
<221> NAME/KEY: CDS
<222> LOCATION: (1)..(27)

<400> SEQUENCE: 5 gag aac gcc ctg cta gtc gcc ctg ttc                                 27
Glu Asn Ala Leu Leu Val Ala Leu Phe
  1               5

<210> SEQ ID NO 6
<211> LENGTH: 9
<212> TYPE: PRT
<213> ORGANISM: Classical Swine Fever Virus
```

<400> SEQUENCE: 6

Glu Asn Ala Leu Leu Val Ala Leu Phe
 1               5

<210> SEQ ID NO 7
<211> LENGTH: 9
<212> TYPE: PRT
<213> ORGANISM: Classical Swine Fever Virus

<400> SEQUENCE: 7

Val Val Gly Leu Ser Thr Ala Glu Asn
 1               5

<210> SEQ ID NO 8
<211> LENGTH: 9
<212> TYPE: PRT
<213> ORGANISM: Classical Swine Fever Virus

<400> SEQUENCE: 8

Val Gly Leu Ser Thr Ala Glu Asn Ala
 1               5

<210> SEQ ID NO 9
<211> LENGTH: 9
<212> TYPE: PRT
<213> ORGANISM: Classical Swine Fever Virus

<400> SEQUENCE: 9

Gly Leu Ser Thr Ala Glu Asn Ala Leu
 1               5

<210> SEQ ID NO 10
<211> LENGTH: 9
<212> TYPE: PRT
<213> ORGANISM: Classical Swine Fever Virus

<400> SEQUENCE: 10

Leu Ser Thr Ala Glu Asn Ala Leu Leu
 1               5

<210> SEQ ID NO 11
<211> LENGTH: 9
<212> TYPE: PRT
<213> ORGANISM: Classical Swine Fever Virus

<400> SEQUENCE: 11

Ser Thr Ala Glu Asn Ala Leu Leu Val
 1               5

<210> SEQ ID NO 12
<211> LENGTH: 9
<212> TYPE: PRT
<213> ORGANISM: Classical Swine Fever Virus

<400> SEQUENCE: 12

Thr Ala Glu Asn Ala Leu Leu Val Ala
 1               5

<210> SEQ ID NO 13
<211> LENGTH: 9
<212> TYPE: PRT
<213> ORGANISM: Classical Swine Fever Virus

<400> SEQUENCE: 13

Ala Glu Asn Ala Leu Leu Val Ala Leu

-continued

<210> SEQ ID NO 14
<211> LENGTH: 9
<212> TYPE: PRT
<213> ORGANISM: Classical Swine Fever Virus

<400> SEQUENCE: 14

Asn Ala Leu Leu Val Ala Leu Phe Gly
 1               5

<210> SEQ ID NO 15
<211> LENGTH: 9
<212> TYPE: PRT
<213> ORGANISM: Classical Swine Fever Virus

<400> SEQUENCE: 15

Ala Leu Leu Val Ala Leu Phe Gly Tyr
 1               5

<210> SEQ ID NO 16
<211> LENGTH: 9
<212> TYPE: PRT
<213> ORGANISM: Classical Swine Fever Virus

<400> SEQUENCE: 16

Leu Leu Val Ala Leu Phe Gly Tyr Val
 1               5

<210> SEQ ID NO 17
<211> LENGTH: 9
<212> TYPE: PRT
<213> ORGANISM: Classical Swine Fever Virus

<400> SEQUENCE: 17

Leu Val Ala Leu Phe Gly Tyr Val Gly
 1               5

<210> SEQ ID NO 18
<211> LENGTH: 15
<212> TYPE: PRT
<213> ORGANISM: Classical Swine Fever Virus

<400> SEQUENCE: 18

Thr Phe Leu Asn Ala Arg Lys Leu Gly Asp Asp Val Pro Pro Tyr
 1               5                  10                  15

<210> SEQ ID NO 19
<211> LENGTH: 15
<212> TYPE: PRT
<213> ORGANISM: Classical Swine Fever Virus

<400> SEQUENCE: 19

Asn Ala Arg Lys Leu Gly Asp Asp Val Pro Pro Tyr Val Tyr Ala
 1               5                  10                  15

<210> SEQ ID NO 20
<211> LENGTH: 15
<212> TYPE: PRT
<213> ORGANISM: Classical Swine Fever Virus

<400> SEQUENCE: 20

Lys Leu Gly Asp Asp Val Pro Pro Tyr Val Tyr Ala Thr Glu Asp
 1               5                  10                  15

```
<210> SEQ ID NO 21
<211> LENGTH: 15
<212> TYPE: PRT
<213> ORGANISM: Classical Swine Fever Virus

<400> SEQUENCE: 21

Asp Asp Val Pro Pro Tyr Val Tyr Ala Thr Glu Asp Glu Asp Leu
 1               5                  10                  15

<210> SEQ ID NO 22
<211> LENGTH: 15
<212> TYPE: PRT
<213> ORGANISM: Classical Swine Fever Virus

<400> SEQUENCE: 22

Pro Pro Tyr Val Tyr Ala Thr Glu Asp Glu Asp Leu Ala Val Glu
 1               5                  10                  15

<210> SEQ ID NO 23
<211> LENGTH: 15
<212> TYPE: PRT
<213> ORGANISM: Classical Swine Fever Virus

<400> SEQUENCE: 23

Val Tyr Ala Thr Glu Asp Glu Asp Leu Ala Val Glu Leu Leu Gly
 1               5                  10                  15

<210> SEQ ID NO 24
<211> LENGTH: 15
<212> TYPE: PRT
<213> ORGANISM: Classical Swine Fever Virus

<400> SEQUENCE: 24

Thr Glu Asp Glu Asp Leu Ala Val Glu Leu Leu Gly Leu Asp Trp
 1               5                  10                  15

<210> SEQ ID NO 25
<211> LENGTH: 14
<212> TYPE: PRT
<213> ORGANISM: Classical Swine Fever Virus

<400> SEQUENCE: 25

Glu Asp Leu Ala Val Glu Leu Leu Gly Leu Asp Trp Pro Asp
 1               5                  10

<210> SEQ ID NO 26
<211> LENGTH: 15
<212> TYPE: PRT
<213> ORGANISM: Classical Swine Fever Virus

<400> SEQUENCE: 26

Ala Val Glu Leu Leu Gly Leu Asp Trp Pro Asp Pro Gly Asn Gln
 1               5                  10                  15

<210> SEQ ID NO 27
<211> LENGTH: 15
<212> TYPE: PRT
<213> ORGANISM: Classical Swine Fever Virus

<400> SEQUENCE: 27

Leu Leu Gly Leu Asp Trp Pro Asp Pro Gly Asn Gln Gly Thr Val
 1               5                  10                  15

<210> SEQ ID NO 28
<211> LENGTH: 15
<212> TYPE: PRT
```

<213> ORGANISM: Classical Swine Fever Virus

<400> SEQUENCE: 28

Leu Asp Trp Pro Asp Pro Gly Asn Gln Gly Thr Val Glu Ala Gly
 1               5                  10                  15

<210> SEQ ID NO 29
<211> LENGTH: 15
<212> TYPE: PRT
<213> ORGANISM: Classical Swine Fever Virus

<400> SEQUENCE: 29

Pro Asp Pro Gly Asn Gln Gly Thr Val Glu Ala Gly Arg Ala Leu
 1               5                  10                  15

<210> SEQ ID NO 30
<211> LENGTH: 17
<212> TYPE: PRT
<213> ORGANISM: Classical Swine Fever Virus

<400> SEQUENCE: 30

Pro Gly Asn Gln Gly Thr Val Glu Ala Gly Arg Ala Leu Lys Gln Val
 1               5                  10                  15

Ser

<210> SEQ ID NO 31
<211> LENGTH: 15
<212> TYPE: PRT
<213> ORGANISM: Classical Swine Fever Virus

<400> SEQUENCE: 31

Gly Thr Val Glu Ala Gly Arg Ala Leu Lys Gln Val Val Gly Leu
 1               5                  10                  15

<210> SEQ ID NO 32
<211> LENGTH: 15
<212> TYPE: PRT
<213> ORGANISM: Classical Swine Fever Virus

<400> SEQUENCE: 32

Glu Ala Gly Arg Ala Leu Lys Gln Val Val Gly Leu Ser Thr Ala
 1               5                  10                  15

<210> SEQ ID NO 33
<211> LENGTH: 15
<212> TYPE: PRT
<213> ORGANISM: Classical Swine Fever Virus

<400> SEQUENCE: 33

Arg Ala Leu Lys Gln Val Val Gly Leu Ser Thr Ala Glu Asn Ala
 1               5                  10                  15

<210> SEQ ID NO 34
<211> LENGTH: 15
<212> TYPE: PRT
<213> ORGANISM: Classical Swine Fever Virus

<400> SEQUENCE: 34

Lys Gln Val Val Gly Leu Ser Thr Ala Glu Asn Ala Leu Leu Val
 1               5                  10                  15

<210> SEQ ID NO 35
<211> LENGTH: 15
<212> TYPE: PRT
<213> ORGANISM: Classical Swine Fever Virus

```
<400> SEQUENCE: 35

Val Gly Leu Ser Thr Ala Glu Asn Ala Leu Leu Val Ala Leu Phe
  1               5                  10                  15

<210> SEQ ID NO 36
<211> LENGTH: 15
<212> TYPE: PRT
<213> ORGANISM: Classical Swine Fever Virus

<400> SEQUENCE: 36

Thr Phe Leu Asn Ala Arg Lys Leu Gly Asp Asp Val Pro Pro Tyr
  1               5                  10                  15
```

We claim:

1. An immunogenic composition against classical swine fever (CSF), comprising CSF virus polypeptide p10 or an immunogenically active part thereof comprising the amino acid sequence of SEQ ID NO:4 or SEQ ID NO:6, together with a pharmaceutically acceptable carrier.

2. The composition according to claim 1, wherein the p10 polypeptide has an amino acid sequence shown in SEQ ID NO:2.

3. An immunogenic composition against classical swine fever (CSF), comprising a recombinant microorganism harboring a DNA molecule encoding CSF virus polypeptide p10, or an immunogenically active part thereof comprising the amino acid sequence of SEQ ID NO:4 or SEQ ID NO:6, together with a pharmaceutically acceptable carrier.

4. The composition according to claim 3, wherein the recombinant microorganism is a recombinant vector virus.

5. The composition according to claim 1, comprising a polypeptide having the amino acid sequence shown in SEQ ID NO:4.

6. The composition according to claim 1, comprising a polypeptide having the amino acid sequence shown in SEQ ID NO:6.

7. The composition according to claim 3, wherein the recombinant microorganism harbors a DNA molecule encoding the amino acid sequence of SEQ ID NO:4.

8. The composition according to claim 3, wherein the recombinant microorganism harbors a DNA molecule encoding the amino acid sequence of SEQ ID NO:6.

9. The composition according to claim 7, wherein the recombinant microorganism is a recombinant vector virus.

10. The composition according to claim 8, wherein the recombinant microorganism is a recombinant vector virus.

11. The composition according to claim 4, wherein the recombinant vector virus is a recombinant pseudorabies virus.

12. The composition according to claim 9, wherein the recombinant vector virus is a recombinant pseudorabies virus.

13. The composition according to claim 10, wherein the recombinant vector virus is a recombinant pseudorabies virus.

* * * * *